(12) United States Patent
Ruan

(10) Patent No.: US 12,077,568 B2
(45) Date of Patent: Sep. 3, 2024

(54) ENGINEERED ACTIVE SINGLE-POLYPEPTIDE CHAIN INSULIN ANALOGS

(71) Applicant: University of Houston System, Houston, TX (US)

(72) Inventor: Ke-He Ruan, Houston, TX (US)

(73) Assignee: University of Houston System, Houston, TX (US)

( * ) Notice: Subject to any disclaimer, the term of this patent is extended or adjusted under 35 U.S.C. 154(b) by 687 days.

(21) Appl. No.: 17/281,870

(22) PCT Filed: Sep. 11, 2019

(86) PCT No.: PCT/US2019/050637
§ 371 (c)(1),
(2) Date: Mar. 31, 2021

(87) PCT Pub. No.: WO2020/072181
PCT Pub. Date: Apr. 9, 2020

(65) Prior Publication Data
US 2021/0388050 A1    Dec. 16, 2021

Related U.S. Application Data

(60) Provisional application No. 62/739,776, filed on Oct. 1, 2018.

(51) Int. Cl.
*C07K 14/62* (2006.01)
*A61K 38/00* (2006.01)
(Continued)

(52) U.S. Cl.
CPC ............... *C07K 14/62* (2013.01); *A61P 3/10* (2018.01); *C12N 15/70* (2013.01); *C12N 15/81* (2013.01);
(Continued)

(58) Field of Classification Search
CPC ... A61K 38/00; A61P 3/08; A61P 3/10; C07K 14/62; C12N 15/70; C12N 15/81; C12N 15/85; C12N 15/86; C12N 2750/14143
See application file for complete search history.

(56) References Cited

U.S. PATENT DOCUMENTS 8,883,449 B2 * 11/2014 Kjeldsen ................... A61P 3/10
435/243
2002/0164712 A1    11/2002 Gan
(Continued)

FOREIGN PATENT DOCUMENTS

WO    WO 2016/057529          4/2016
WO    WO-2017041001 A2 *   3/2017 ............. A61K 38/28

OTHER PUBLICATIONS

Koonin et al., Chapter 2 Evolutionary Concept in Genetics and Genomics, Sequence—Evolution—Function: Computational Approaches in Comparative Genomics. Boston: Kluwer Academic; 2003; NCBI Bookshelf; attached as pdf, 25 pages (Year: 2003).*

(Continued)

*Primary Examiner* — Randall L Beane
(74) *Attorney, Agent, or Firm* — Parker Highlander PLLC

(57) ABSTRACT

Described herein are single chain polypeptides comprising both the b- and a-chains of insulin fused to each other by a linker. Also provided are nucleic acids coding for the same, host cells expressing the same, and methods of use therefor.

13 Claims, 13 Drawing Sheets

Figure 2A:
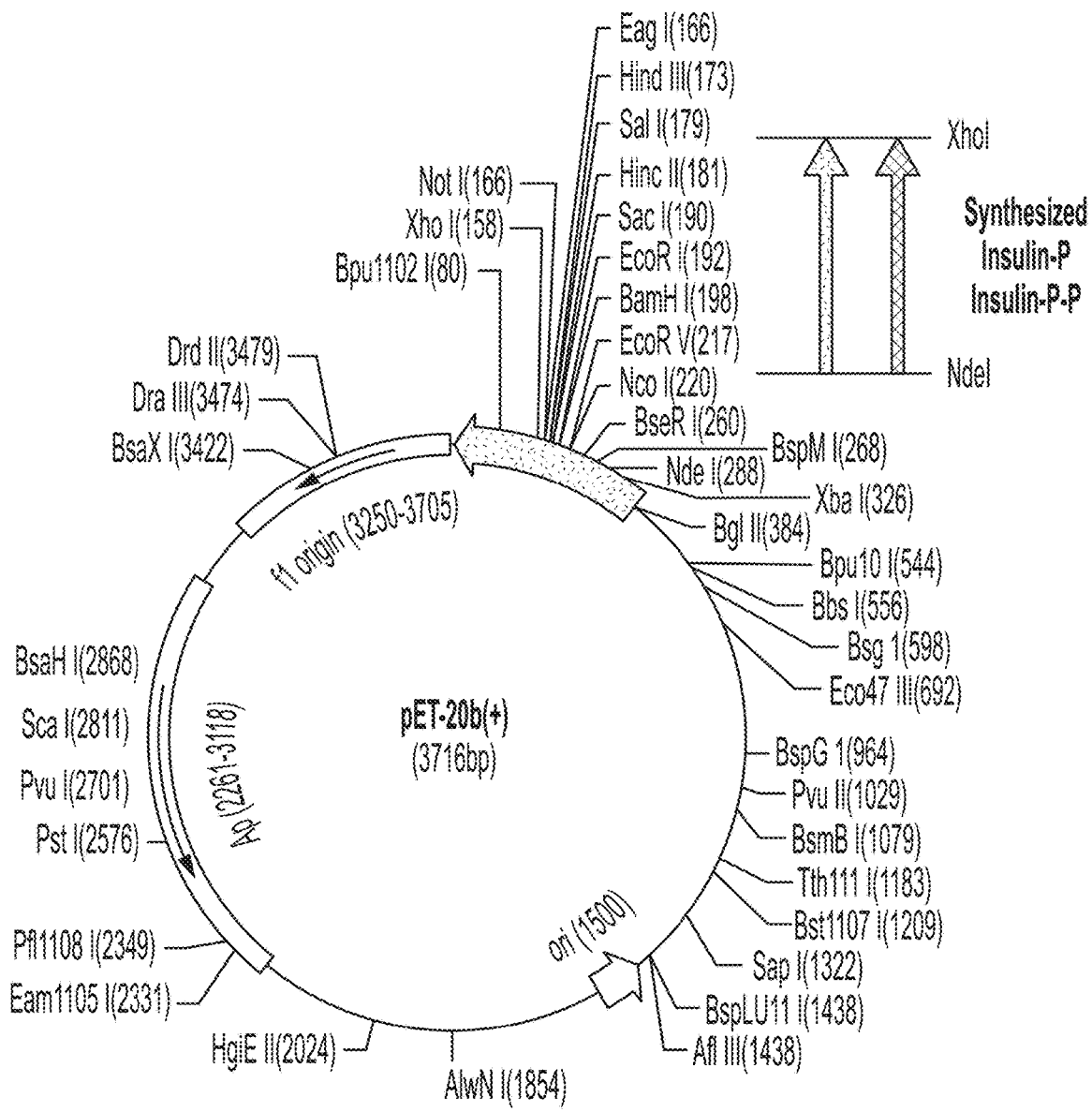

Specification includes a Sequence Listing.

SPC-insulin-P Sequence

NdeI
CATATGTTCGTGAACCAGCATCTGTGTGGCAGCCATCTGGTGGAGGCGCTGTATCTGGTGTGTGGCGAGCGCGGC
    M  F  V  N  Q  H  L  C  G  S  H  L  V  E  A  L  Y  L  V  C  G  E  R  G
TTCTTCTACACTCCGAAGACTCCTGGCATCGTGGAGCAGTGCTGCACCAGCATCTGCAGCCTGTATCAGCTGGAG
 F  F  Y  T  P  K  T  P  G  I  V  E  Q  C  C  T  S  I  C  S  L  Y  Q  L  E
AACTACTGCAACTGACTCGAG
 N  Y  C  N  *  XhoI

(51) Int. Cl.
A61P 3/10       (2006.01)
C12N 15/70      (2006.01)
C12N 15/81      (2006.01)
C12N 15/85      (2006.01)
C12N 15/86      (2006.01)

(52) U.S. Cl.
CPC .............. C12N 15/85 (2013.01); C12N 15/86 (2013.01); A61K 38/00 (2013.01); C12N 2750/14143 (2013.01)

(56) References Cited

U.S. PATENT DOCUMENTS

2008/0139481 A1*  6/2008  Dix ..................... A61P 29/02
                                                   514/12.4
2016/0074534 A1   3/2016  Bosch Tubert et al.

OTHER PUBLICATIONS

Webber et al.. Genes and homology, Current Biology, vol. 14(9):R:332-R333 (May 4, 2004) (Year: 2004).*
Rost, Twilight zone of protein sequence alignments, Protein Engineering, vol. 12(2):85-94 (1999) (Year: 1999).*
Wagner et al., New Naturally Occurring Amino Acids, Anew. Chem. Int. Ed. Engl. 22:816-828 (1983) (Year: 1983).*
GenBank AAC78289.1, proinsulin-like protein BKRA [synthetic construct], NCBI.nlm.nih.gov, 1 page (Nov. 18, 1998), also available at https://www.ncbi.nlm.nih.gov/protein/AAC78289.1 (last visited Jan. 25, 2024) (Year: 1998).*
NP_001278826.1, insulin preproprotein [Homo sapiens], NCBI, 3 pages (PRI Jan. 9, 2024), also available at https://www.ncbi.nlm.nih.gov/protein/NP_001278826.1 (last visited Jan. 26, 2024) (Year: 2024).*
Livingstone et al., Protein sequence alignments, Cabios, vol. 9(6):745-756 (1993) (Year: 1993).*
Aggarwal, S. R., "What's fueling the biotech engine-2011 to 2012," *Nature Biotechnology*, 30 (2012): 1191-1197.
Baeshen, N. A. et al., "Cell factories for insulin production," *Microbial Cell Factories*, 13 (2014): 1-9.
Brems, D. N. et al., "Altering the association properties of insulin by amino acid replacement," *Protein Eng.*, 5.6 (1992): 527-533.
Kaur, Z. P. et al., "Discovery of high potency, single-chain insulin analogs with a shortened B-chain and nonpeptide linker," *ACS Chem Biology*, 8.8 (2013): 1822-1829.
Nakagawa, S. H. et al., "Perturbation of insulin-receptor interactions by intramolecular hormone cross-linking: Analysis of relative movement among residues A1, B1, and B29," *Journal of Biological Chemistry*, 264.1 (1989): 272-279.
PCT International Preliminary Report on Patentability issued in International Patent Application No. PCT/US2019/050637, dated Apr. 15, 2021.
PCT International Search Report and Written Opinion issued in International Patent Application No. PCT/US2019/050637, dated Dec. 4, 2019.
Tof, I. et al., "Recombinant DNA technology in the synthesis of human insulin," *Little Tree Publishing*, (1994): 1-12.
"Remembering First Successful Laboratory Production of Human Insulin Announced." *News Release, Genentech*, (1978): 1-4.
Zhang, X.-Z. et al., "Simple, fast and high-efficiency transformation system for directed evolution of cellulase in *Bacillus subtilis*," *Microbial Biotechnology*, (2010): 1-8.

* cited by examiner

SPC-insulin-P Sequence

NdeI
CATATGTTCGTGAACCAGCATCTGTGTGGCAGCCATCTGGTGGAGGCGCTGTATCTGGTGTGTGGCGAGCGCGGC
 M  F  V  N  Q  H  L  C  G  S  H  L  V  E  A  L  Y  L  V  C  G  E  R  G
TTCTTCTACACTCCGAAGACTCCTGGCATCGTGGAGCAGTGCTGCACCAGCATCTGCAGCCTGTATCAGCTGGAG
 F  F  Y  T  P  K  T  P  G  I  V  E  Q  C  C  T  S  I  C  S  L  Y  Q  L  E
AACTACTGCAACTGACTCGAG
 N  Y  C  N  *  XhoI

FIG. 1A

SPC-insulin-PP Sequence

NdeI
CATATGTTCGTGAACCAGCATCTGTGTGGCAGCCATCTGGTGGAGGCGCTGTATCTGGTGTGTGGCGAGCGCGGC
 M  F  V  N  Q  H  L  C  G  S  H  L  V  E  A  L  Y  L  V  C  G  E  R  G
TTCTTCTACACTCCGAAGACTCCTCCGGGCATCGTGGAGCAGTGCTGCACCAGCATCTGCAGCCTGTATCAGCTG
 F  F  Y  T  P  K  T  P  P  G  I  V  E  Q  C  C  T  S  I  C  S  L  Y  Q  L
GAGAACTACTGCAACTGACTCGAG
 E  N  Y  C  N  *  XhoI

FIG. 1B

ENGINEERED ACTIVE SINGLE-POLYPEPTIDE CHAIN INSULIN ANALOGS

PRIORITY CLAIM

This application is a national phase application under 35 U.S.C. § 371 of International Application No. PCT/US2019/050637, filed Sep. 11, 2019, which claims benefit of priority to U.S. Provisional Application Ser. No. 62/739,776, filed Oct. 1, 2018, the entire contents of each of which are hereby incorporated by reference.

BACKGROUND

I. Field

The present disclosure relates to the fields of endocrinology, protein biology, recombinant protein engineering and expression and medicine. More specifically, the disclosure relates to single chain polypeptide insulin molecules with improved properties for in vivo glucose regulation.

II. Related Art

The importance of insulin for human disease treatment has been well-recognized. World Health Organization (WHO) has listed insulin as one of Essential Medicines, a basic medicine for health system (19th WHO Model List of Essential Medicines, 2015). With the increasing of diabetes patients worldwide, the market of insulin is continually increasing. Zion Market Research has predicted a market for insulin reached to 43.6 billion in 2021 (Zion Market, worldwide-web at zionmarketresearch.com/news/global-human-insulin-market).

Insulin has been well-characterized and widely used to treat diabetes and other diseases since it was discovered by Banting and Best in 1921 (The Nobel Prize in Physiology or Medicine 1923). Insulin is a polypeptide hormone biosynthesized by pancreatic beta cells and released into blood circulation constantly. It is one of major anabolic hormones promoting biosynthesis of carbohydrates, lipids and proteins, to lower the elevated blood glucose level resulted from physiological conditions (such as, after meals) and pathological conditions (such as, diabetes). Deficiency of insulin produced from the beta cells will cause an opposite effect of anabolic, promoting catabolisms of carbohydrate, lipid and proteins to increase blood glucose level (Voet D., 2011; Koeslag et al., 2003). Type 1 diabetes is caused by the loss of the major function of the beta cells, which can no longer to synthesize and secrete insulin into the blood circulation (Koeslag et al., 2003). Type 2 diabetes shows insulin resistance in peripheral tissues, but also shows the partial loss of insulin production ability of the beta cells. Insulin therapy is required for type 1 diabetes and is suitable for type 2 diabetes. Due to the insulin resistance, type-2 diabetes needs higher doses of insulin compared to that of type 1 diabetes in general.

The active wild-type (regular) human insulin with a molecular mass of 5808 Da is composed of 51 amino acid resides formed by two polypeptide chains, a-chain (21 amino acid residues) and b-chain (30 amino acid residues). The disulfide-bonds linked the a- and b-chains are readily reduced to separate the active insulin into inactive a-chain and b-chain in the circulation. This is one of the reasons resulted that the free insulin in circulation has short half-life (4-6 minutes) in vivo (Duckworth et al., 1998). This has also determined the needs of the inconvenient multiple-injections of regular insulin for diabetes patients daily.

Today, recombinant DNA technology using E. coli and yeast expression systems have become a major approach to produce large quantities of human insulin for clinic uses. [Drug Information Portal NLM—Insulin human USAN, 1978, druginfo.nlm.nih.gov/drugportal/; Tof I 1994; Aggarwal 2012; Baeshen, et al., 2014; Chance, et al., 1993; Chance, et al. 1999; Kjeldsen 2000). In addition, human insulin analogs aimed to have fast- or long-acting than that of the regular insulin are also available for clinic uses. For examples, HumaLog (insulin Lispro), Apidra and NovoRapid have been developed as fast acting insulins by preventing dimer and hexamer formation, led to start a rapid effect (in 15 minutes) after injection (Howey, et al. 1994; Mudaliar, et al 1999). But, the acting duration of those wild-type insulin has only 4-8 hours. The long acting insulin, such as insulin Glargine (for slow release by addition of an amino acid, arginine residues to the b-chain to reducing the solubility at physiological pH) and insulin Detemir (for slow release by addition of myristic acid to C-terminal position of insulin b-chain) have steady effects for 18-24 hours. However, all of the commercial insulin and analogs remain the property readily reduced into inactive a- and b-chains once they are free in circulation.

Recently, chemically synthesized single-chain insulin analogs have also been reported but are not yet in the market. For example, the insulin analogs covalently linked the a-chain N-terminus to a site proximal to the b-chain C-terminus by linkers contained 2-12 atoms of aliphatic dicarboxylic acid had been reported. However, the analogs could only remain 2-40% of native insulin activity (Nakagawa, et al. 1989). Modification of the proinsulin using a C-peptide sequence, GGGPGRR and four mutations in the a- and b-chain (HisA8, AspB10, AspB28, and ProB29) to mimic insulin-like Growth Factor 1 (IGF-1) has been reported (Brems, et al., 1992). Kaur Z P. et al reported that synthetic insulin analog by shortened b-chain and using of different sizes of polyethylene glycol(PEG) to chemically replaced C-peptide of insulin were able to remain the insulin biological actives (Kaur et al., 2013). Those chemical synthesis approaches required to add chemical groups into the polypeptide chains of insulin, which may cause side effects, and not suitable for recombinant production. Recombinant proinsulin with shorter sizes of C-peptide sequences have also been reported (Baeshen N A, et al. 2014). However, it remains as inactive proinsulin and the method is only suitable for increasing the biosynthesis yield.

SUMMARY

As noted above, wild-type active insulin has two-chain configuration linked by disulfide bonds, which are readily reduced into inactive a- and b-chains once the insulin is free in circulation. This means insulin has very short half-life (4-6 mins) and requires multiple injections daily to lower elevated glucose for diabetic patients. To address this issue, in this disclosure the a- and b-chain polypeptides of the wild-type insulin were covalently linked together using the optimized amino-acid linker to form newly engineered single polypeptide chain (SPC)-insulins, which is longer acting and therefore highly suitable for clinical use. In the preparation, a cDNA coding of the C-terminus of the b-chain peptide of insulin is linked to the cDNA coding of the N-terminus of the a-chain peptide of insulin by a bridge coding for one or two amino acid residues, such as proline. Transfection of E. coli and yeast (Saccharomyces cerevisiae)

cells using the engineered cDNAs resulted in recombinantly expressed SPC-insulins that could not be separated into inactive two-chains, resulting in an increased duration of action. In testing on normal and Streptozotocin (STZ)-induced type-1 diabetic mice, the SPC-insulins showed an active duration of up to 24-48 hours, which is 3-5-fold longer than that of the regular insulin, such as Humulin R. This active SPC-insulin thus has great potentiated to be used as a replacement or an addition to existing insulins and insulin analogs to treat type-1 and -2 diabetes. The creating of SPC-insulins also provides a basic structure to be further modified into even longer and/or rapid acting forms using single-polypeptide chain techniques.

Thus, in one embodiment, there is provided a single chain polypeptide having biological activity comprising both the b- and a-chain of insulin connected by an amino acid linker connecting the b-chain to the a-chain. The b-chain C-terminus may be connected through the linker to the N-terminus of the a-chain, or the a-chain C-terminus may be connected through the linker to the N-terminus of the b-chain. The linker may comprise or consist of 1-8 natural or non-natural amino acids, and more specifically may comprise or consist of 1 or 2 proline residues. The polypeptide may comprise or consist of the sequence shown in FIG. 1A or FIG. 1B, or a polypeptide having 90% or more homology to the sequence shown in FIG. 1A or FIG. 1B, or polypeptide having 95% or more homology to the sequence shown in FIG. 1A or FIG. 1B.

In another embodiment, there is provided an expression cassette comprising a nucleic acid encoding the polypeptide as defined above under the control of a promoter. The promoter may be a bacterial promoter or a eukaryotic promoter, such as a yeast promoter, a human promoter, an animal promoter, an insect promoter or a plant promoter. The expression cassette may further be comprised in a replicable expression construct, such as a viral expression construct, such as an AAV viral vector. The replicable expression construct may be a non-viral expression construct, such as a pET20b vector for *E. coli* expression, or a pYES2 vector for yeast expression, or pcDNA3.1 vector for mammalian cell expression.

Also provided is a host cell comprising the expression cassette as described above. The host cell may be a bacterial cell, such as *E. coli*, or a eukaryotic cell, such as a yeast cell, such as *S. cerevisiae*, a plant cell, an insect cell, such as a *Spodoptera frugiperda* cell, an animal cell, a human cell, such as a fat cell, a stem cell, a smooth muscle cell, an endothelial cell, a pancreatic cell, a liver cell, a kidney cell, a brain cell, a gastro-intestinal cell, a skin cell, a bone cell, a heart cell, a vascular cell, or a tumor cell, or a plant cell, such as a tobacco cell. The host cell may be selectively susceptible to killing by an exogenous agent that will not harm normal human or animal cells. The host cell may be contained in an implantable device.

In another embodiment, there is provided a method of treating diabetes or hyperglycemia in a subject comprising administering to said subject the single chain polypeptide, the expression cassette, or the host cell as defined above. The method may further comprise administering to said subject wild-type insulin. The subject maybe a human or a non-human animal, such as a dog, a cat, a horse, a cow, a sheep, a rabbit or a mouse. Administering may comprise multiple injections of the single chain polypeptide, or stable expression of the single chain polypeptide from the expression cassette or host cell following transfer.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-B. cDNA and amino acid sequences of SPC-insulins newly created. The sequences of a-chain and b-chain of wild-type human insulin were covalently linked together by one (FIG. 1A; nucleic acid=SEQ ID NO: 1; amino acid=SEQ ID NO: 2) or two (FIG. 1B; nucleic acid=SEQ ID NO: 3; amino acid=SEQ ID NO:4) amino acid residues using proline residue (P) as an example (see boxed P or PP). The sites of Ndel and XHoI designed for cDNA cloning are showed.

FIGS. 2A-B. Subcloning of the cDNAs of SPC-insulins into expressing vectors. (FIG. 2A) *E. coli* expression vector, pET-20b(+) with an insert of the cDNA of SPC-insulin-P or SPC-insulin-PP, and (FIG. 2B) Yeast expression vector, pYES2 with an insert of the SPC-insulin-P or SPC-insulin-PP.

FIGS. 3A-B. SDS-PAGE (sodium dodecyl sulfate-polyacrylamide gel electrophoresis) analysis of the yeast expressed SPC-insulins. (FIG. 3A) Crude culture medium of yeast cells expressing SPC-insulins. (FIG. 3B) One-step Sepharose G-75 purified SPC-insulins. 5 (purified) or 50 μg (unpurified) of proteins were separated by denatured 15% SDS-PAGE and then stained with Coomassie Blue. The crude (FIG. 3A) and purified (FIG. 3B) SPC-insulins were shown. 50 μg of Humulin R insulin was used as positive control.

FIGS. 4A-D. MALDI-TOF mass spectrometric analysis for yeast-expressed SPC-insulins. The expressed SPC-insulins (approximately 20-25 ng/each, FIGS. 4A and 4B) released into their culture media were isolated by Sephadex G-75 column. The second peak contained SPC-insulins were analyzed by MALDI-TOF mass spectrometry. The Humulin R (approximately 250 ng) was used as positive control (FIG. 4C). Western Blot analysis of the SPC-insulins (20-25 μg/each) and Humulin R (24 μg) was performed using Anti-proinsulin antibody on 15% SDS-PAGE (FIG. 4D).

FIGS. 5A-C. (FIG. 5A) Time course of expression of SPC-insulins using *E. coli* system. 50 μg of proteins collected from different time of the *E. coli* expression was analyzed by 15% SDS-PAGE, and then stained by Coommasie blue. (FIG. 5B) Elution profile of the SPC-Insulin purification from Sephadex G-75 column (1.5×50 cm) using PBS buffer. The fractions within the peaks showing weak (+)

or strong (+++) biological activities were labeled. (FIG. 5C) SDS-PAGE analysis of the expressed SPC-insulins using *E. coli* system. 50 μg (unpurified, lane 2 (SPC-insulin-P) and 3 (SPC-insulin-PP)) or purified (lane 4 (SPC-insulin-P) and 5 (SPC-insulin-PP)) of proteins were separated by 15% SDS-PAGE and then stained with Coomassie Blue. 50 μg of Humulin R was used as positive control (lane 1).

Figure 6A:
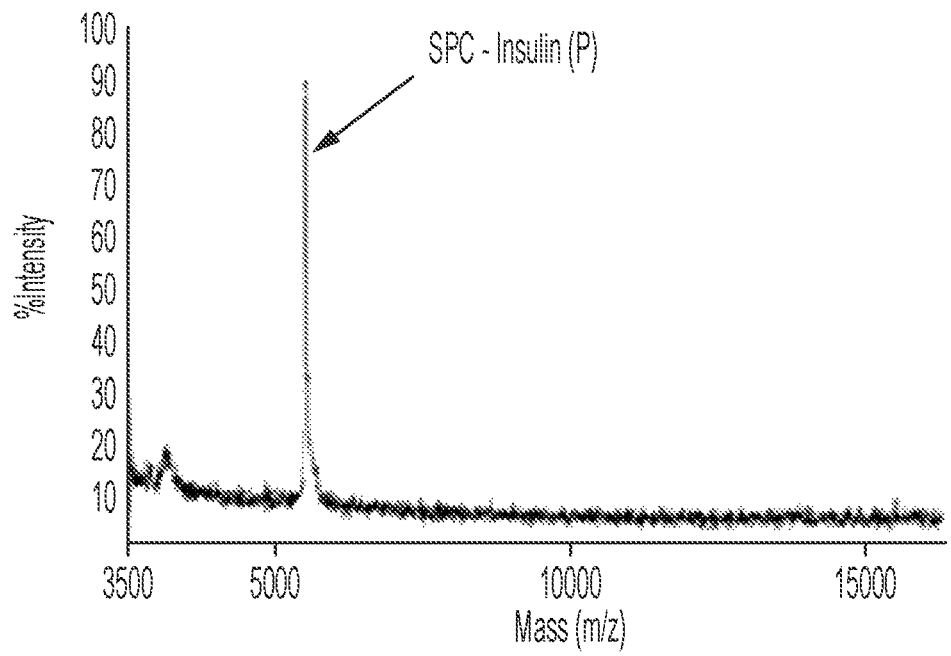
Figure 6B:
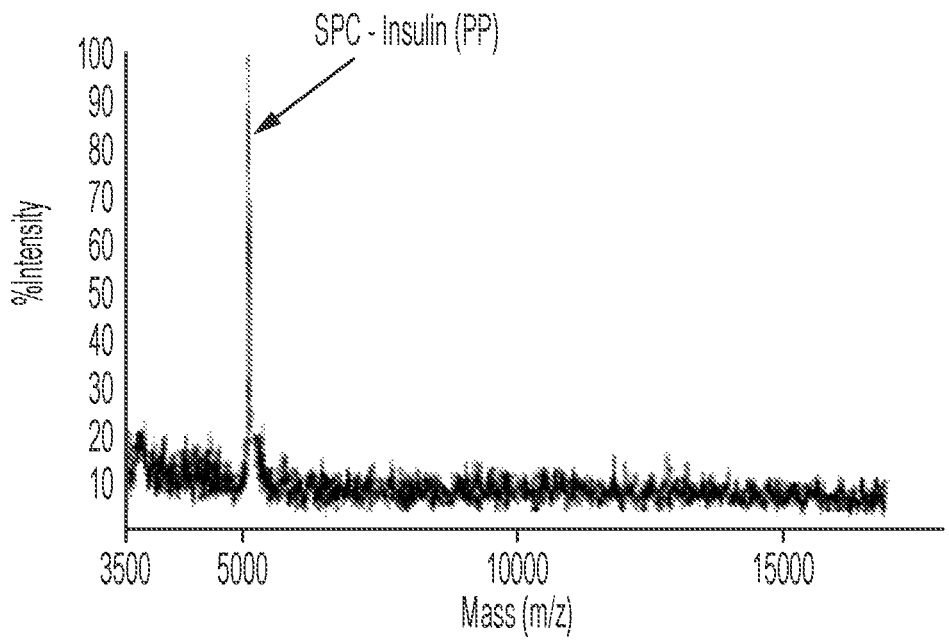
Figure 6C:
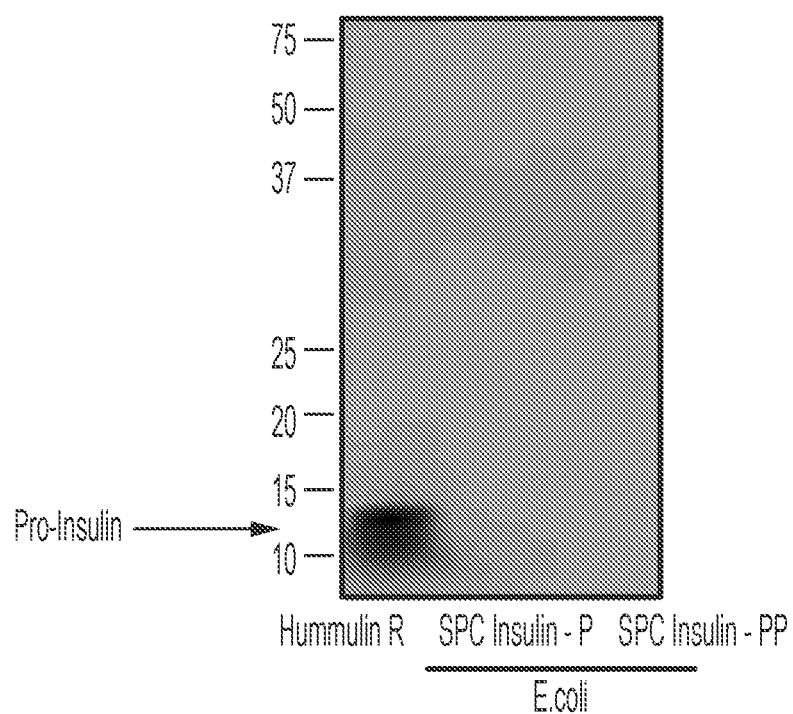

FIGS. 6A-C. MALDI-TOF mass spectrometric analysis for *E. coli*-expressed SPC-insulins. The expressed SPC-insulins (approximately 20-25 ng/each, FIGS. 6A-B) were isolated from *E. coli* and purified by ion-exchange column and Sephadex G-75 columns. The second peak from the G75 column contained SPC-insulins were analyzed by MALDI-TOF mass spectrometry (FIGS. 6A-B). The. Western Blot analysis of the purified *E. coli*-expressed SPC-insulins (20-25 μg/each) and Humulin R (24 μg) was performed using Anti-proinsulin antibody on 15% SDS-PAGE (C).

Figure 7A:
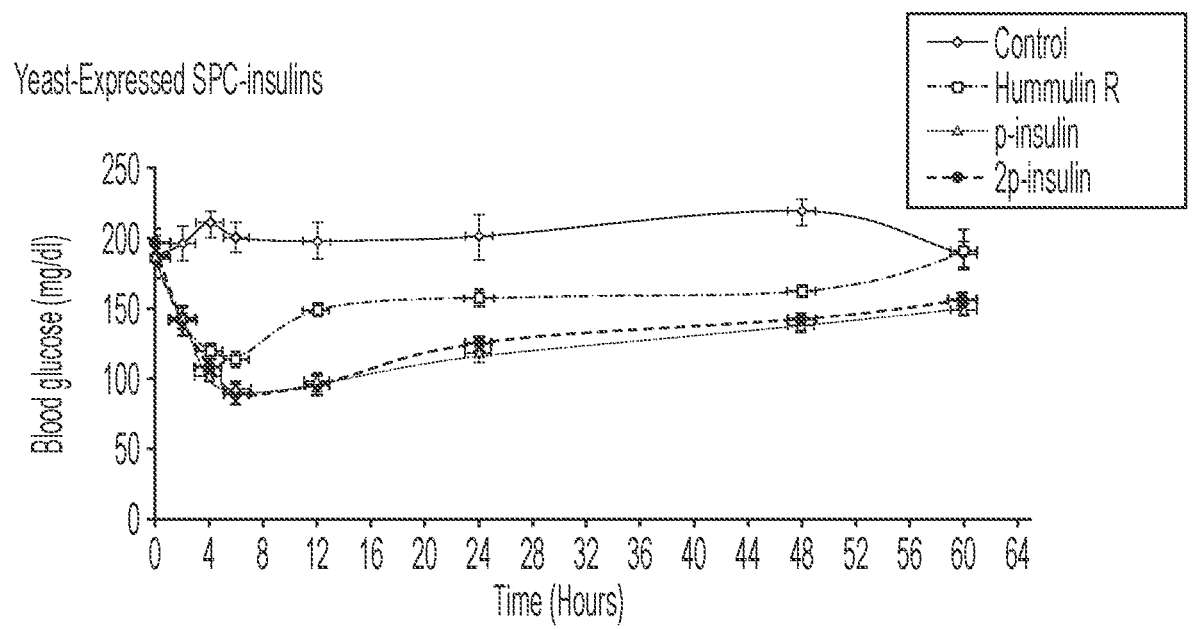
Figure 7B:
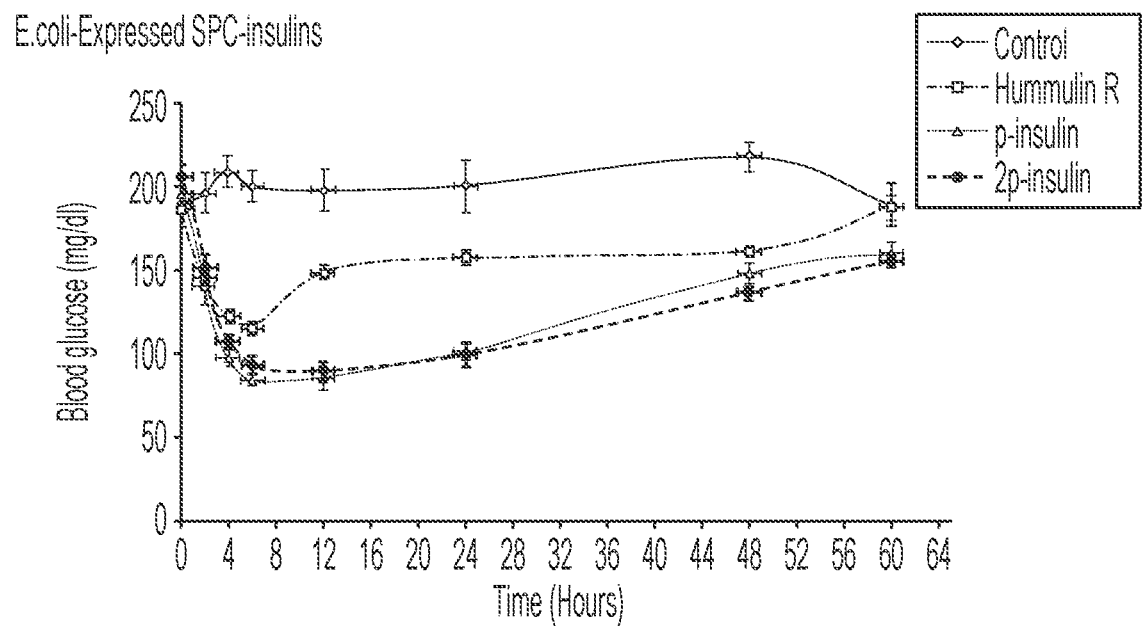

FIGS. 7A-B. Effect of SPC-insulins on lowering blood glucose level in vivo. The purified yeast-(FIG. 7A) or *E. coli*-(FIG. 7B) expressed SPC-insulin-P (p-insulin) and SPC-insulin-PP (2p-insulin) (20-24 μg/mouse) was injected (intraperitoneally) into normal mice. The glucose levels of the blood collected from tail vein at the increasing time points were measured using Contour$^{next}$ One glucose meter (n=6). Humulin R (20-24 μg/mouse) was used as a positive control (n=6, M±SE). The mice were under normal diets.

Figure 8A:
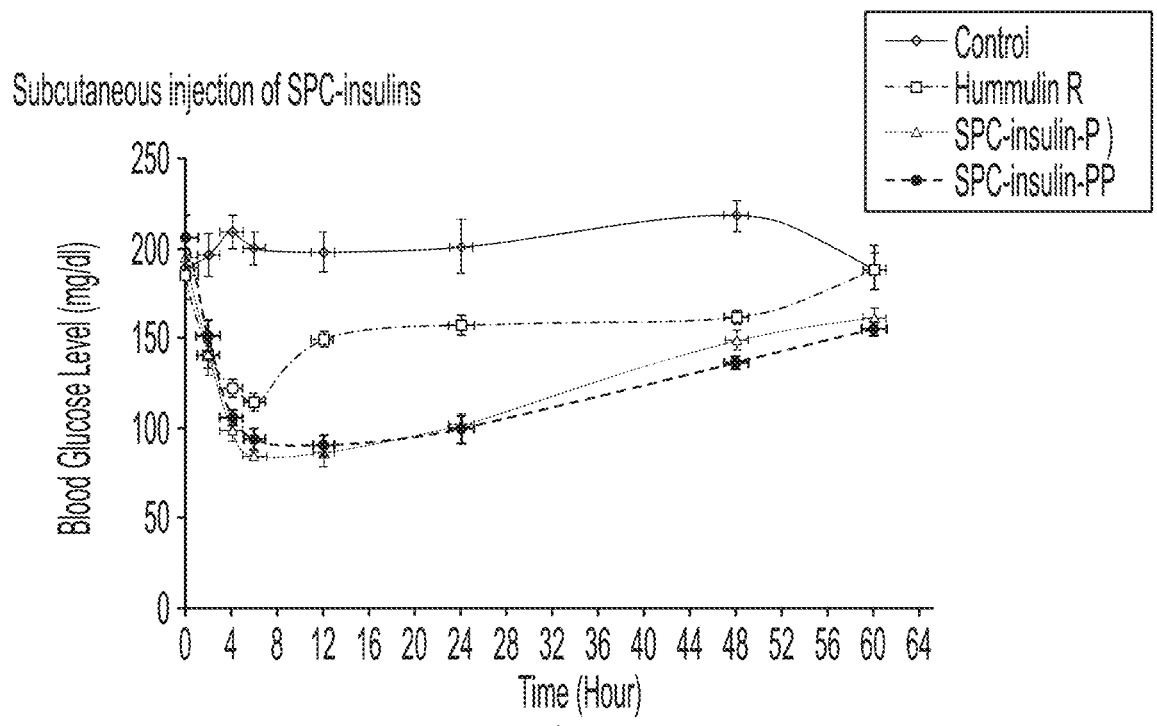
Figure 8B:
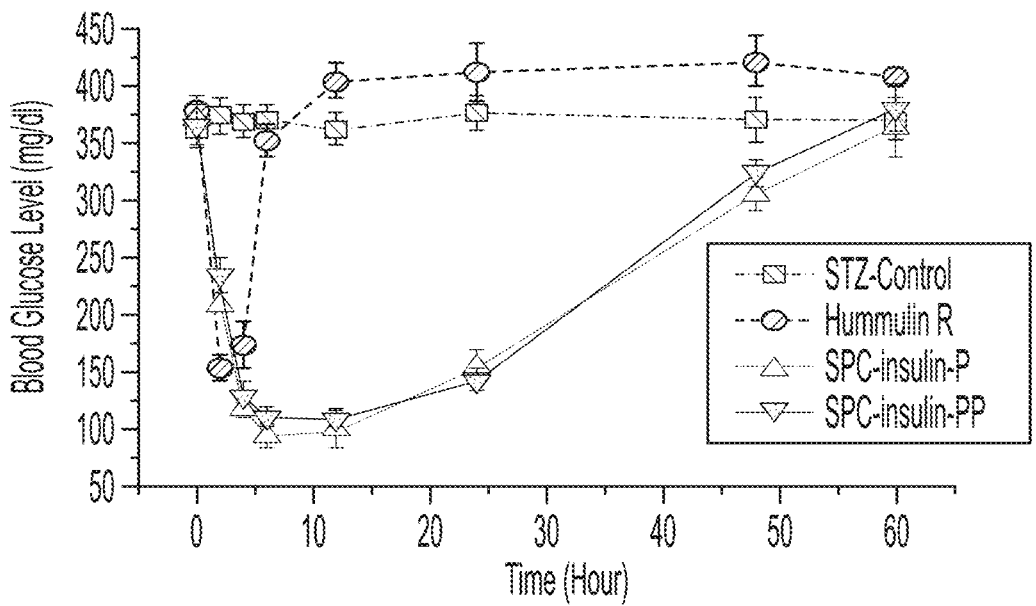

FIGS. 8A-B. (FIG. 8A) Effect of SPC-insulins on lowering blood glucose level of normal mice using subcutaneous injection. The yeast-expressed SPC-insulin-P (p-insulin) and SPC-insulin-PP (2p-insulin) (20-30 μg/mouse) was injected subcutaneously into the normal mice (n=6). (FIG. 8B) Effects of the purified *E. coli*-expressed SPC-insulins on lowering blood glucose level of STZ-induced type-1 diabetic mice. 20-30 μg/mouse of the purified *E. coli*-expressed SPC-P (P-insulin) or SPC-insulin-PP (PP-insulin) was intraperitoneally injected into the STZ-induced Type-1 diabetic mice (with an elevated blood glucose levels of 370-400 mg/dl, n=6). The glucose levels of the blood collected from the mouse tail vein at the increasing time points were measured using Contour$^{next}$ One glucose meter. Humulin R (20-24 μg/mouse) was used as a positive control (n=6, M±SE). STZ-Control=oval; Hummulin R=rectangle; SPC-Insulin-P=upward pointing triangle; SPC-Insulin-PP=downward pointing triangle.

DETAILED DESCRIPTION

All active insulin and insulin analogs in the market have two chains, which can be easily reduced into inactive individual a- and b-chains, resulted a very short half-life (4-6 minis) once the insulin molecule becomes free form in the plasma. The inventors have created SPC-insulins having both insulin chains combined in a single polypeptide chain Thus, SPC-insulins have longer acting than that of the parent two chain insulins to their inherent resistance to reduction in vivo Animal experiments have confirmed that the SPC-insulins can effectively lower blood sugar level up to 24-48 hours, which is much longer than that of 4-8 hours of the unmodified regular two-chain insulins in the market. The SPC-insulins can be easily produced using recombinant protein approaches (such as, *E. coli* and yeast expression systems), as well as single-polypeptide chemical synthesis. Current recombinant two-chain insulin production requires at least two steps, producing and purification of inactive proinsulin as step one, and enzymatic removal of the C-peptide and further purification of the matured insulin as step two. The invented method is a one-step production of the active recombinant insulin, which is not only simplified, but eliminates the possibility of contamination of the inactive proinsulin with degraded a- and b-chains during production. This advance has also made it possible to directly produce active insulin instead of proinsulin in cells and tissues using gene delivery approach in vitro and in vivo.

These and other aspects of the disclosure are set out in detail below.

I. DIABETES

Diabetes mellitus (DM), commonly referred to as diabetes, is a group of metabolic disorders in which there are high blood sugar levels over a prolonged period. Symptoms of high blood sugar include frequent urination, increased thirst, and increased hunger. If left untreated, diabetes can cause many complications. Acute complications can include diabetic ketoacidosis, hyperosmolar hyperglycemic state, or death. Serious long-term complications include cardiovascular disease, stroke, chronic kidney disease, foot ulcers, and damage to the eyes.

Prediabetes indicates a condition that occurs when a person's blood glucose levels are higher than normal but not high enough for a diagnosis of type 2 DM. Many people who later develop type 2 DM spend many years in a state of prediabetes. In contrast, diabetes is due to either the pancreas not producing enough insulin, or the cells of the body not responding properly to the insulin produced. There are three main types of diabetes mellitus:

Type 1 DM results from the pancreas's failure to produce enough insulin due to loss of beta cells. This form was previously referred to as "insulin-dependent diabetes mellitus" (IDDM) or "juvenile diabetes". The cause is unknown.

Type 2 DM begins with insulin resistance, a condition in which cells fail to respond to insulin properly. As the disease progresses a lack of insulin may also develop. This form was previously referred to as "non-insulin-dependent diabetes mellitus" (NIDDM) or "adult-onset diabetes". The most common cause is excessive body weight and insufficient exercise.

Gestational diabetes is the third main form and occurs when pregnant women without a previous history of diabetes develop high blood sugar levels.

There are other causes of diabetes, however. For example, maturity onset diabetes of the young (MODY) is an autosomal dominant inherited form of diabetes, due to one of several single-gene mutations causing defects in insulin production. It is significantly less common than the three main types. The name of this disease refers to early hypotheses as to its nature. Being due to a defective gene, this disease varies in age at presentation and in severity according to the specific gene defect; thus there are at least 13 subtypes of MODY. People with MODY often can control it without using insulin.

Latent autoimmune diabetes of adults (LADA) is a condition in which type 1 DM develops in adults. Adults with LADA are frequently initially misdiagnosed as having type 2 DM, based on age rather than cause.

Some cases of diabetes are caused by the body's tissue receptors not responding to insulin (even when insulin levels are normal, which is what separates it from type 2 diabetes); this form is very uncommon. Genetic mutations (autosomal or mitochondrial) can lead to defects in beta cell function. Abnormal insulin action may also have been genetically determined in some cases. Any disease that causes extensive damage to the pancreas may lead to diabetes (for example, chronic pancreatitis and cystic fibrosis). Diseases associated with excessive secretion of insulin-antagonistic hormones can cause diabetes (which is typically resolved once the hormone excess is removed). Many drugs impair insulin secretion and some toxins damage pancreatic beta cells.

Other forms of diabetes mellitus include congenital diabetes, which is due to genetic defects of insulin secretion, cystic fibrosis-related diabetes, steroid diabetes induced by high doses of glucocorticoids, and several forms of monogenic diabetes.

Prevention and treatment involve maintaining a healthy diet, regular physical exercise, a normal body weight, and avoiding use of tobacco. Control of blood pressure and maintaining proper foot care are important for people with the disease. Type 1 DM must be managed with insulin injections. Type 2 DM may be treated with medications with or without insulin. Insulin and some oral medications can cause low blood sugar. Weight loss surgery in those with obesity is sometimes an effective measure in those with type 2 DM. Gestational diabetes usually resolves after the birth of the baby.

As of 2015, an estimated 415 million people had diabetes worldwide, with type 2 DM making up about 90% of the cases. This represents 8.3% of the adult population, with equal rates in both women and men. As of 2014, trends suggested the rate would continue to rise. Diabetes at least doubles a person's risk of early death. From 2012 to 2015, approximately 1.5 to 5.0 million deaths each year resulted from diabetes. The global economic cost of diabetes in 2014 was estimated to be US$ 612 billion. In the United States, diabetes cost 245 billion in 2012.

II. INSULIN

Insulin is a peptide hormone produced by beta cells of the pancreatic islets; it is considered to be the main anabolic hormone of the body. It regulates the metabolism of carbohydrates, fats and protein by promoting the absorption of carbohydrates, especially glucose from the blood into liver, fat and skeletal muscle cells. In these tissues the absorbed glucose is converted into either glycogen via glycogenesis or fats (triglycerides) via lipogenesis, or, in the case of the liver, into both. Glucose production and secretion by the liver is strongly inhibited by high concentrations of insulin in the blood. Circulating insulin also affects the synthesis of proteins in a wide variety of tissues. It is therefore an anabolic hormone, promoting the conversion of small molecules in the blood into large molecules inside the cells. Low insulin levels in the blood have the opposite effect by promoting widespread catabolism, especially of reserve body fat.

Beta cells are sensitive to glucose concentrations, also known as blood sugar levels. When the glucose level is high, the beta cells secrete insulin into the blood; when glucose levels are low, secretion of insulin is inhibited. Their neighboring alpha cells, by taking their cues from the beta cells, secrete glucagon into the blood in the opposite manner: increased secretion when blood glucose is low, and decreased secretion when glucose concentrations are high. Glucagon, through stimulating the liver to release glucose by glycogenolysis and gluconeogenesis, has the opposite effect of insulin. The secretion of insulin and glucagon into the blood in response to the blood glucose concentration is the primary mechanism of glucose homeostasis.

If beta cells are destroyed by an autoimmune reaction, insulin can no longer be synthesized or be secreted into the blood. This results in type 1 diabetes mellitus, which is characterized by abnormally high blood glucose concentrations, and generalized body wasting. In type 2 diabetes mellitus the destruction of beta cells is less pronounced than in type 1 diabetes and is not due to an autoimmune process. Instead, there is an accumulation of amyloid in the pancreatic islets, which likely disrupts their anatomy and physiology. The pathogenesis of type 2 diabetes is not well understood but patients exhibit a reduced population of islet beta-cells, reduced secretory function of islet beta-cells that survive, and peripheral tissue insulin resistance. Type 2 diabetes is characterized by high rates of glucagon secretion into the blood which are unaffected by, and unresponsive to the concentration of glucose in the blood. Insulin is still secreted into the blood in response to the blood glucose. As a result, the insulin levels, even when the blood sugar level is normal, are much higher than they are in healthy persons.

The human insulin protein is composed of 51 amino acids, and has a molecular mass of 5808 Da. It is a dimer of an A-chain and a B-chain, which are linked together by disulfide bonds. Insulin's structure varies slightly between species of animals. Insulin from animal sources differs somewhat in effectiveness (in carbohydrate metabolism effects) from human insulin because of these variations. Porcine insulin is especially close to the human version and was widely used to treat type 1 diabetics before human insulin could be produced in large quantities by recombinant DNA technologies. The crystal structure of insulin in the solid state was determined by Dorothy Hodgkin. It is on the WHO Model List of Essential Medicines, the most important medications needed in a basic health system. The preproinsulin precursor of insulin is encoded by the INS gene. A variety of mutant alleles with changes in the coding region have been identified. A read-through gene, INS-IGF2, overlaps with this gene at the 5' region and with the IGF2 gene at the 3' region.

In the pancreatic β cells, glucose is the primary physiological stimulus for the regulation of insulin synthesis. Insulin is mainly regulated through the transcription factors PDX1, NeuroD1, and MafA. PDX1 (Pancreatic and duodenal homeobox protein 1) is in the nuclear periphery upon low blood glucose levels interacting with corepressors HDAC1 and 2 which is downregulating the insulin secretion. An increase in blood glucose levels causes phosphorylation of PDX1 and it translocates centrally and binds the A3 element within the insulin promoter. Upon translocation it interacts with coactivators HAT p300 and acetyltransferase set 7/9. PDX1 affects the histone modifications through acetylation and deacetylation as well as methylation. It is also said to suppress glucagon.

NeuroD1, also known as (β2, regulates insulin exocytosis in pancreatic β cells by directly inducing the expression of genes involved in exocytosis. It is localized in the cytosol, but in response to high glucose it becomes glycosylated by OGT and/or phosphorylated by ERK, which causes translocation to the nucleus. In the nucleus β2 heterodimerizes with E47, binds to the E1 element of the insulin promoter and recruits co-activator p300 which acetylates β2. It is able to interact with other transcription factors as well in activation of the insulin gene.

MafA is degraded by proteasomes upon low blood glucose levels. Increased levels of glucose make an unknown protein glycosylated. This protein works as a transcription factor for MafA in an unknown manner and MafA is transported out of the cell. MafA is then translocated back into the nucleus where it binds the C1 element of the insulin promoter.

These transcription factors work synergistically and in a complex arrangement. Increased blood glucose can after a while destroy the binding capacities of these proteins, and therefore reduce the amount of insulin secreted, causing diabetes. The decreased binding activities can be mediated by glucose induced oxidative stress and antioxidants are said to prevent the decreased insulin secretion in glucotoxic pancreatic β cells. Stress signaling molecules and reactive oxygen species inhibits the insulin gene by interfering with the cofactors binding the transcription factors and the transcription factors itself.

Several regulatory sequences in the promoter region of the human insulin gene bind to transcription factors. In general, the A-boxes bind to Pdx1 factors, E-boxes bind to NeuroD, C-boxes bind to MafA, and cAMP response elements to CREB. There are also silencers that inhibit transcription.

Within vertebrates, the amino acid sequence of insulin is strongly conserved. Bovine insulin differs from human in only three amino acid residues, and porcine insulin in one. Even insulin from some species of fish is similar enough to human to be clinically effective in humans. Insulin in some invertebrates is quite similar in sequence to human insulin and has similar physiological effects. The strong homology seen in the insulin sequence of diverse species suggests that it has been conserved across much of animal evolutionary history. The C-peptide of proinsulin (discussed later), however, differs much more among species; it is also a hormone, but a secondary one.

The primary structure of bovine insulin was first determined by Frederick Sanger in 1951. After that, this polypeptide was synthesized independently by several groups. The 3-dimensional structure of insulin was determined by X-ray crystallography in Dorothy Hodgkin's laboratory in 1969 (PDB file 1 ins).

Insulin is produced and stored in the body as a hexamer (a unit of six insulin molecules), while the active form is the monomer. The hexamer is an inactive form with long-term stability, which serves as a way to keep the highly reactive insulin protected, yet readily available. The hexamer-monomer conversion is one of the central aspects of insulin formulations for injection. The hexamer is far more stable than the monomer, which is desirable for practical reasons; however, the monomer is a much faster-reacting drug because diffusion rate is inversely related to particle size. A fast-reacting drug means insulin injections do not have to precede mealtimes by hours, which in turn gives people with diabetes more flexibility in their daily schedules. Insulin can aggregate and form fibrillar interdigitated beta-sheets. This can cause injection amyloidosis and prevents the storage of insulin for long periods.

A. Synthesis, Release and Degradation

Insulin is produced in the pancreas and the Brockmann body (in some fish), and released when any of several stimuli are detected. These stimuli include ingested protein and glucose in the blood produced from digested food. Carbohydrates can be polymers of simple sugars or the simple sugars themselves. If the carbohydrates include glucose, then that glucose will be absorbed into the bloodstream and blood glucose level will begin to rise. In target cells, insulin initiates a signal transduction, which has the effect of increasing glucose uptake and storage. Finally, insulin is degraded, terminating the response.

In mammals, insulin is synthesized in the pancreas within the beta cells. One million to three million pancreatic islets form the endocrine part of the pancreas, which is primarily an exocrine gland. The endocrine portion accounts for only 2% of the total mass of the pancreas. Within the pancreatic islets, beta cells constitute 65-80% of all the cells.

Insulin consists of two polypeptide chains, the A- and B-chains, linked together by disulfide bonds. It is however first synthesized as a single polypeptide called preproinsulin in beta cells. Preproinsulin contains a 24-residue signal peptide which directs the nascent polypeptide chain to the rough endoplasmic reticulum (RER). The signal peptide is cleaved as the polypeptide is translocated into lumen of the RER, forming proinsulin. In the RER the proinsulin folds into the correct conformation and 3 disulfide bonds are formed. About 5-10 min after its assembly in the endoplasmic reticulum, proinsulin is transported to the trans-Golgi network (TGN) where immature granules are formed. Transport to the TGN may take about 30 min.

Proinsulin undergoes maturation into active insulin through the action of cellular endopeptidases known as prohormone convertases (PC1 and PC2), as well as the exoprotease carboxypeptidase E. The endopeptidases cleave at 2 positions, releasing a fragment called the C-peptide, and leaving 2 peptide chains, the B- and A-chains, linked by 2 disulfide bonds. The cleavage sites are each located after a pair of basic residues (lysine-64 and arginine-65, and arginine-31 and -32). After cleavage of the C-peptide, these 2 pairs of basic residues are removed by the carboxypeptidase. The C-peptide is the central portion of proinsulin, and the primary sequence of proinsulin goes in the order "B-C-A" (the B and A chains were identified on the basis of mass and the C-peptide was discovered later).

The resulting mature insulin is packaged inside mature granules waiting for metabolic signals (such as leucine, arginine, glucose and mannose) and vagal nerve stimulation to be exocytosed from the cell into the circulation.

The endogenous production of insulin is regulated in several steps along the synthesis pathway: at transcription from the insulin gene, in mRNA stability, at the mRNA translation, and in the post-translational modifications.

Beta cells in the islets of Langerhans release insulin in two phases. The first-phase release is rapidly triggered in response to increased blood glucose levels, and lasts about 10 minutes. The second phase is a sustained, slow release of newly formed vesicles triggered independently of sugar, peaking in 2 to 3 hours. Reduced first-phase insulin release may be the earliest detectable beta cell defect predicting onset of type 2 diabetes. First-phase release and insulin sensitivity are independent predictors of diabetes.

The description of first phase release is as follows. Glucose enters the (β-cells through the glucose transporters, GLUT2. These glucose transporters have a relatively low affinity for glucose, ensuring that the rate of glucose entry into the (β-cells is proportional to the extracellular glucose concentration (within the physiological range). At low blood sugar levels, very little glucose enters the (β-cells; at high blood glucose concentrations large quantities of glucose enter these cells.

The glucose that enters the (β-cell is phosphorylated to glucose-6-phosphate (G-6-P) by glucokinase (hexokinase IV) which is not inhibited by G-6-P in the way that the hexokinases in other tissues (hexokinase I—III) are affected by this product. This means that the intracellular G-6-P concentration remains proportional to the blood sugar concentration. Glucose-6-phosphate enters glycolytic pathway and then, via the pyruvate dehydrogenase reaction, into the Krebs cycle, where multiple, high-energy ATP molecules are produced by the oxidation of acetyl CoA (the Krebs cycle substrate), leading to a rise in the ATP:ADP ratio within the cell.

An increased intracellular ATP:ADP ratio closes the ATP-sensitive SUR1/Kir6.2 potassium channel (see sulfonylurea receptor). This prevents potassium ions (K+) from leaving the cell by facilitated diffusion, leading to a buildup of intracellular potassium ions. As a result, the inside of the cell becomes less negative with respect to the outside, leading to the depolarization of the cell surface membrane. Upon depolarization, voltage-gated calcium ion ($Ca^{2+}$) channels open, allowing calcium ions to move into the cell by facilitated diffusion. The cytosolic calcium ion concentration can also be increased by calcium release from intracellular stores via activation of ryanodine receptors.

The calcium ion concentration in the cytosol of the beta cells can also, or additionally, be increased through the activation of phospholipase C resulting from the binding of an extracellular ligand (hormone or neurotransmitter) to a G protein-coupled membrane receptor. Phospholipase C cleaves the membrane phospholipid, phosphatidyl inositol 4,5-bisphosphate, into inositol 1,4,5-trisphosphate and diacylglycerol. Inositol 1,4,5-trisphosphate (IP3) then binds to receptor proteins in the plasma membrane of the endoplasmic reticulum (ER). This allows the release of $Ca^{2+}$ ions from the ER via IP3-gated channels, which raises the cytosolic concentration of calcium ions independently of the effects of a high blood glucose concentration. Parasympathetic stimulation of the pancreatic islets operates via this pathway to increase insulin secretion into the blood.

The significantly increased amount of calcium ions in the cells' cytoplasm causes the release into the blood of previously synthesized insulin, which has been stored in intracellular secretory vesicles. This is the primary mechanism for release of insulin. Other substances known to stimulate insulin release include the amino acids arginine and leucine, parasympathetic release of acetylcholine (acting via the phospholipase C pathway), sulfonylurea, cholecystokinin (CCK, also via phospholipase C), and the gastrointestinally derived incretins, such as glucagon-like peptide-1 (GLP-1) and glucose-dependent insulinotropic peptide (GIP).

Release of insulin is strongly inhibited by norepinephrine (noradrenaline), which leads to increased blood glucose levels during stress. It appears that release of catecholamines by the sympathetic nervous system has conflicting influences on insulin release by beta cells, because insulin release is inhibited by $\alpha_2$-adrenergic receptors and stimulated by $\beta_2$-adrenergic receptors. The net effect of norepinephrine from sympathetic nerves and epinephrine from adrenal glands on insulin release is inhibition due to dominance of the $\alpha$-adrenergic receptors.

When the glucose level comes down to the usual physiologic value, insulin release from the β-cells slows or stops. If the blood glucose level drops lower than this, especially to dangerously low levels, release of hyperglycemic hormones (most prominently glucagon from islet of Langerhans alpha cells) forces release of glucose into the blood from the liver glycogen stores, supplemented by gluconeogenesis if the glycogen stores become depleted. By increasing blood glucose, the hyperglycemic hormones prevent or correct life-threatening hypoglycemia.

Evidence of impaired first-phase insulin release can be seen in the glucose tolerance test, demonstrated by a substantially elevated blood glucose level at 30 minutes after the ingestion of a glucose load (75 or 100 g of glucose), followed by a slow drop over the next 100 minutes, to remain above 120 mg/100 ml after two hours after the start of the test. In a normal person the blood glucose level is corrected (and may even be slightly over-corrected) by the end of the test.

Once an insulin molecule has docked onto the receptor and effected its action, it may be released back into the extracellular environment, or it may be degraded by the cell. The two primary sites for insulin clearance are the liver and the kidney. The liver clears most insulin during first-pass transit, whereas the kidney clears most of the insulin in systemic circulation. Degradation normally involves endocytosis of the insulin-receptor complex, followed by the action of insulin-degrading enzyme. An insulin molecule produced endogenously by the beta cells is estimated to be degraded within about one hour after its initial release into circulation (insulin half-life~4-6 minutes).

B. Physiological Effects

The actions of insulin on the global human metabolism level include increase of cellular intake of certain substances, most prominently glucose in muscle and adipose tissue (about two-thirds of body cells), increase of DNA replication and protein synthesis via control of amino acid uptake, and modification of the activity of numerous enzymes.

The actions of insulin (indirect and direct) on cells include:

Stimulates the uptake of glucose—Insulin decreases blood glucose concentration by inducing intake of glucose by the cells. This is possible because Insulin causes the insertion of the GLUT4 transporter in the cell membranes of muscle and fat tissues which allows glucose to enter the cell.

Increased fat synthesis—insulin forces fat cells to take in blood glucose, which is converted into triglycerides; decrease of insulin causes the reverse. Increased esterification of fatty acids—forces adipose tissue to make neutral fats (i.e., triglycerides) from fatty acids; decrease of insulin causes the reverse.

Decreased lipolysis—forces reduction in conversion of fat cell lipid stores into blood fatty acids and glycerol; decrease of insulin causes the reverse. Induce glycogen synthesis—When glucose levels are high, insulin induces the formation of glycogen by the activation of the hexokinase enzyme, which adds a phosphate group in glucose, thus resulting in a molecule that cannot exit the cell. At the same time, insulin inhibits the enzyme glucose-6-phosphatase, which removes the phosphate group. These two enzymes are key for the formation of glycogen. Also, insulin activates the enzymes phosphofructokinase and glycogen synthase which are responsible for glycogen synthesis.

Decreased gluconeogenesis and glycogenolysis—decreases production of glucose from noncarbohydrate substrates, primarily in the liver (the vast majority of endogenous insulin arriving at the liver never leaves the liver); increase of insulin causes glucose production by the liver from assorted substrates.

Decreased proteolysis—decreasing the breakdown of protein

Decreased autophagy—decreased level of degradation of damaged organelles. Postprandial levels inhibit autophagy completely.

Increased amino acid uptake—forces cells to absorb circulating amino acids; decrease of insulin inhibits absorption.

Arterial muscle tone—forces arterial wall muscle to relax, increasing blood flow, especially in microarteries; decrease of insulin reduces flow by allowing these muscles to contract.

Increase in the secretion of hydrochloric acid by parietal cells in the stomach.

Increased potassium uptake—forces cells synthesizing glycogen (a very spongy, "wet" substance, that increases the content of intracellular water, and its accompanying $K^+$ ions) to absorb potassium from the extracellular fluids; lack of insulin inhibits absorption. Insulin's increase in cellular potassium uptake lowers potassium levels in blood plasma. This possibly occurs via insulin-induced translocation of the Na+/K+-ATPase to the surface of skeletal muscle cells.

Decreased renal sodium excretion.

Insulin also influences other body functions, such as vascular compliance and cognition. Once insulin enters the human brain, it enhances learning and memory and benefits verbal memory in particular Enhancing brain insulin signaling by means of intranasal insulin administration also enhances the acute thermoregulatory and glucoregulatory response to food intake, suggesting that central nervous insulin contributes to the co-ordination of a wide variety of homeostatic or regulatory processes in the human body. Insulin also has stimulatory effects on gonadotropin-releasing hormone from the hypothalamus, thus favoring fertility.

C. Medical Uses

Biosynthetic human insulin (insulin human rDNA, INN) for clinical use is manufactured by recombinant DNA technology. Biosynthetic human insulin has increased purity when compared with extractive animal insulin, enhanced purity reducing antibody formation. Researchers have succeeded in introducing the gene for human insulin into plants as another method of producing insulin ("biopharming") in safflower. This technique is anticipated to reduce production costs.

Several analogs of human insulin are available. These insulin analogs are closely related to the human insulin structure and were developed for specific aspects of glycemic control in terms of fast action (prandial insulins) and long action (basal insulins). The first biosynthetic insulin analog was developed for clinical use at mealtime (prandial insulin), Humalog (insulin lispro), it is more rapidly absorbed after subcutaneous injection than regular insulin, with an effect 15 minutes after injection. Other rapid-acting analogues are NovoRapid and Apidra, with similar profiles. All are rapidly absorbed due to amino acid sequences that will reduce formation of dimers and hexamers (monomeric insulins are more rapidly absorbed). Fast acting insulins do not require the injection-to-meal interval previously recommended for human insulin and animal insulins. The other type is long acting insulin; the first of these was Lantus (insulin glargine). These have a steady effect for an extended period from 18 to 24 hours. Likewise, another protracted insulin analogue (Levemir) is based on a fatty acid acylation approach. A myristic acid molecule is attached to this analogue, which associates the insulin molecule to the abundant serum albumin, which in turn extends the effect and reduces the risk of hypoglycemia. Both protracted analogues need to be taken only once daily and are used for type 1 diabetics as the basal insulin. A combination of a rapid acting and a protracted insulin is also available, making it more likely for patients to achieve an insulin profile that mimics that of the body's own insulin release.

Insulin is usually taken as subcutaneous injections by single-use syringes with needles, via an insulin pump, or by repeated-use insulin pens with disposable needles. Inhaled insulin is also available in the U.S. market now. Synthetic insulin can trigger adverse effects, so some people with diabetes rely on animal-source insulin.

Unlike many medicines, insulin currently cannot be taken orally because, like nearly all other proteins introduced into the gastrointestinal tract, it is reduced to fragments, whereupon all activity is lost. There has been some research into ways to protect insulin from the digestive tract, so that it can be administered orally or sublingually.

III. SPC INSULINS

The present disclosure, in one aspect, relates to the production and formulation of single chain protein insulins as well as their delivery to cells, tissues or subjects. The insulin chains may be obtained from human, dog, cat, horse, cow, sheep, rabbit, mouse, rat, primate or other mammalian source. In general, recombinant production of proteins is well known and is therefore not described in detail here. The discussion of nucleic acids and expression vectors, found below, is however incorporated in this discussion.

The single chain polypeptide comprises both the b- and a-chain of insulin connected by an amino acid linker. It will have the biological activity of wild-type insulin, i.e., binding to the insulin receptor, signaling through the insulin receptor, and the ability to regulate glucose levels in vivo. connecting the C-terminus of the b-chain to the N-terminus of the a-chain. The orientation of the chains may be a-chain followed by a linker followed by b-chain, or b-chain followed by a linker followed by a-chain. The linker may comprise or consist of 1-8 natural or non-natural amino acids, and in particular employs prolines, such as 1 or 2 proline residues. Reference is made to exemplary sequences shown in FIG. 1A or FIG. 1B. Some variation is permitted while retaining biological activity, and therefore the inventors envision a polypeptide having 90% or more, 95% or more, or 99% or more homology to the sequence shown in FIG. 1A or FIG. 1B.

A. Purification of Proteins

It will be desirable to purify proteins according to the present disclosure. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present disclosure concern the purification, and in particular embodiments, the substantial purification, of an encoded protein or peptide. The term "purified protein" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein composition that has been subjected to fractionation to remove various other components, and which composition substantially retains its expressed biological activity. Where the term "substantially purified" is used, this designation will refer to a composition in which the protein forms the major component of the composition, such as constituting about 50%, about 60%, about 70%, about 80%, about 90%, about 95% or more of the proteins in the composition.

Various methods for quantifying the degree of purification of the protein will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low-pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-Acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present disclosure is discussed below.

B. Protein Delivery

Because insulin binds to a receptor, formulation for therapeutic use is straightforward. However, while not required, formulation in delivery vehicles such as liposomes and nanoparticles is contemplated. For example, liposomes, which are artificially prepared vesicles made of lipid bilayers have been used to deliver a variety of drugs. Liposomes can be composed of naturally-derived phospholipids with mixed lipid chains (like egg phosphatidylethanolamine) or other surfactants. In particular, liposomes containing cationic or neutral lipids have been used in the formulation of drugs. Liposomes should not be confused with micelles and reverse micelles composed of monolayers, which also can be used for delivery. A wide variety of commercial formulations for protein delivery are well known including PULSin™, Lipodin-Pro, Carry-MaxR, Pro-DeliverIN, PromoFectin, Pro-Ject, Chariot™ Protein Delivery reagent, BioPORTER™, and others.

Nanoparticles are generally considered to be particulate substances having a diameter of 100 nm or less. In contrast to liposomes, which are hollow, nanoparticles tend to be solid. Thus, the drug will be less entrapped and more either embedded in or coated on the nanoparticle. Nanoparticles can be made of metals including oxides, silica, polymers such as polymethyl methacrylate, and ceramics. Similarly, nanoshells are somewhat larger and encase the delivered substances with these same materials. Either nanoparticles or nanoshells permit sustained or controlled release of the peptide or mimetic and can stabilize it to the effects of in vivo environment.

C. Therapeutic Formulations

Where clinical applications are contemplated, pharmaceutical compositions will be prepared in a form appropriate for the intended application. Generally, this will entail preparing compositions that are essentially free of pyrogens, as well as other impurities that could be harmful to humans or animals One will generally desire to employ appropriate salts and buffers to render drugs, proteins or delivery vectors stable and allow for uptake by target cells. Aqueous compositions of the present disclosure comprise an effective amount of the vector or protein, dissolved or dispersed in a pharmaceutically acceptable carrier or aqueous medium.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the vectors or cells of the compositions.

The active compositions of the present disclosure may include classic pharmaceutical preparations. Administration of these compositions according to the present disclosure may be via any common route so long as the target tissue is available via that route. This includes oral, nasal, or buccal. Alternatively, administration may be by intradermal, subcutaneous, intramuscular, intraperitoneal or intravenous injection, or intra-arterial injection. Such compositions would normally be administered as pharmaceutically acceptable compositions, as described supra.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present disclosure generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered, and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

IV. NUCLEIC ACID CONSTRUCTS

As discussed above, in certain embodiments, applicants contemplate recombinant expression of SPC-insulin, and expression cassettes/constructs are employed to express this product, either for subsequent purification and delivery to a cell/subject, or for use directly in a genetic-based delivery approach. Expression requires that appropriate signals be provided in the vectors and include various regulatory elements such as enhancers/promoters from both viral and mammalian sources that drive expression of the genes of interest in cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

A. Regulatory Elements

Throughout this application, the term "expression cassette" is meant to include any type of genetic construct containing a nucleic acid coding for a gene product in which part or all of the nucleic acid encoding sequence is capable of being transcribed and translated, i.e., is under the control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. An "expression vector" is meant to include expression cassettes comprised in a genetic construct that is capable of replication, and thus including one or more of origins of replication, transcription termination signals, poly-A regions, selectable markers, and multipurpose cloning sites.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best-known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, viral promotes such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters/enhancers and inducible promoters/enhancers that could be used in combination with the nucleic acid encoding a gene of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

Promoter and/or Enhancer

| Promoter/Enhancer | References |
|---|---|
| Immunoglobulin Heavy Chain | Banerji et al., 1983; Gilles et al., 1983; Grosschedl and Baltimore, 1985; Atchinson et al., 1986, 1987; Imler et al., 1987; Weinberger et al., 1984; Kiledjian et al., 1988; Porlon et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |

TABLE 1-continued

| Promoter and/or Enhancer | |
|---|---|
| Promoter/Enhancer | References |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tranche et al., 1989, 1990 |
| α-Fetoprotein | Godbout et al., 1988; Campere et al., 1989 |
| t-Globin | Bodine & Ley, 1987; Perez-Stable et al., 1990 |
| β-Globin | Trudel et al. ,1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr and Clarke., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell & Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

| Inducible Elements | | |
|---|---|---|
| Element | Inducer | References |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |

TABLE 2-continued

Inducible Elements

| Element | Inducer | References |
|---|---|---|
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Where a cDNA insert is employed, one will typically desire to include a polyadenylation signal to effect proper polyadenylation of the gene transcript. The nature of the polyadenylation signal is not believed to be crucial to the successful practice of the disclosure, and any such sequence may be employed such as human growth hormone and SV40 polyadenylation signals. Also contemplated as an element of the expression cassette is a terminator. These elements can serve to enhance message levels and to minimize read through from the cassette into other sequences.

B. Delivery of Expression Vectors

There are a number of ways in which expression vectors may introduced into cells. In certain embodiments of the disclosure, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1-liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the disclosure. The adenovirus may be of any of the 42 different known serotypes or subgroups A-F. Adenovirus type 5 of subgroup C is the preferred starting material in order to obtain the conditional replication-defective adenovirus vector for use in the present disclosure. This is because Adenovirus type 5 is a human adenovirus about which a great deal of biochemical and genetic information is known, and it has historically been used for most constructions employing adenovirus as a vector.

As stated above, the typical vector according to the present disclosure is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the disclosure. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present disclosure. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact- sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present disclosure. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present disclosure. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell, the nucleic acid encoding the SPC-insulin be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the disclosure, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the disclosure for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present disclosure.

In a further embodiment of the disclosure, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection. A reagent known as Lipofectamine 2000™ is widely used and commercially available.

In certain embodiments of the disclosure, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present disclosure. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

IV. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Design and Synthesis of SPC-Insulin cDNAs 1-1. Design of SPC-Insulins Using a Linker with One or Two Amino Acid Residue(s).

The newly designed SPC-insulins were based on the structural information of human insulin. The cDNA and polypeptide sequences are shown in FIGS. 1A-B. The calculated molecular weights of the human SPC-insulin-P and -PP are 6024 Da and 6121 Da, respectively.

1-2. Preparation of the cDNAs of the SPC-Insulins.

The designed cDNA sequences for SPC-insulin-P (FIG. 1A) and SPC-insulin-PP (FIG. 1B) were prepared using following steps. The cDNA coding region of b-chain of human insulin was linked to the cDNA coding region of a-chain of human insulin by a cDNA coding for a single (FIG. 1A) amino acid residue (Proline) or for two amino acid residues (Proline-Proline), to form single-chain cDNA sequences of SPC-insulin-P (FIG. 1A) and SPC-insulin-PP (FIG. 1B). The entire cDNA sequences were synthesized by DNA synthesis method.

Example 2

Producing of the Engineered SPC-Insulins Using Yeast (*Saccharomyces cerevisiae*) System 2-1. Preparation of Yeast Expression Vector:

The cDNA of SPC-insulins (SPC-insulin-P and SPC-insulin-PP) were inserted into the cutting sites between HindIII and BamH1 of a yeast vector, pYES2 as shown in FIG. 2A. The success cloning was confirmed by DNA sequencing.

2-2. Expression of the SPC-Insulins Using the Yeast Cells.

Figure 3A:
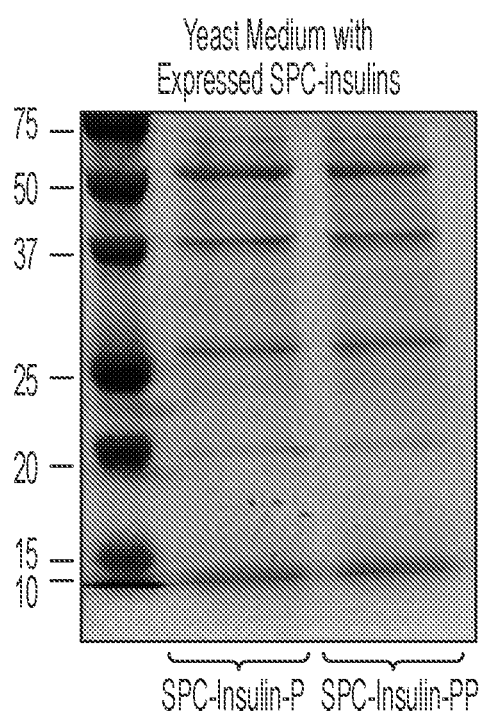

Expression of the SPC-insulin-P and -PP in yeast system was established by transfection of the yeast cells using pYES2 vectors containing the cDNA of SPC-insulin-P or SPC-insulin-PP followed by culturing the recipient cells under conditions supporting protein synthesis. The expressed SPC-insulins secreted into culture medium was observed after 15-20 hours' induction (FIG. 3A).

2-3. One-Step Purification of SPC-Insulins from the Yeast Culture Medium.

Figure 3B:
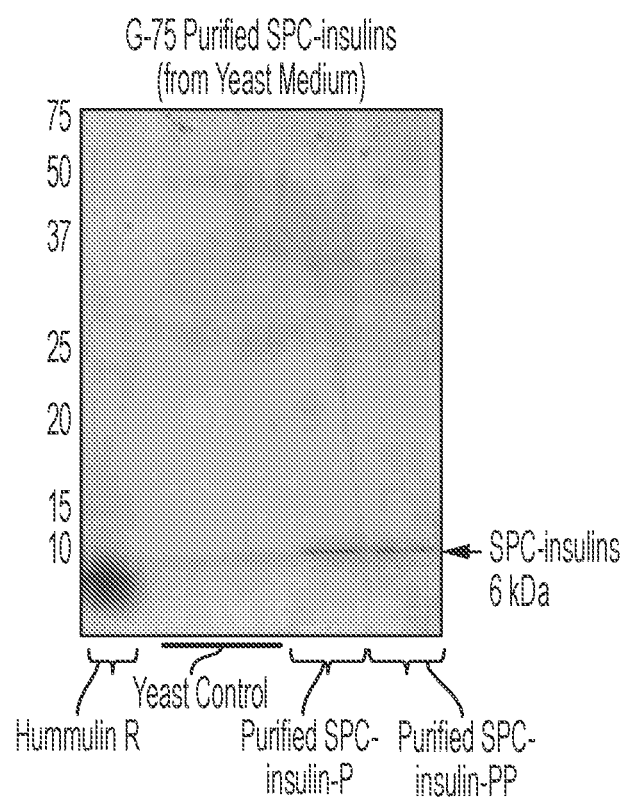
Figure 4A:
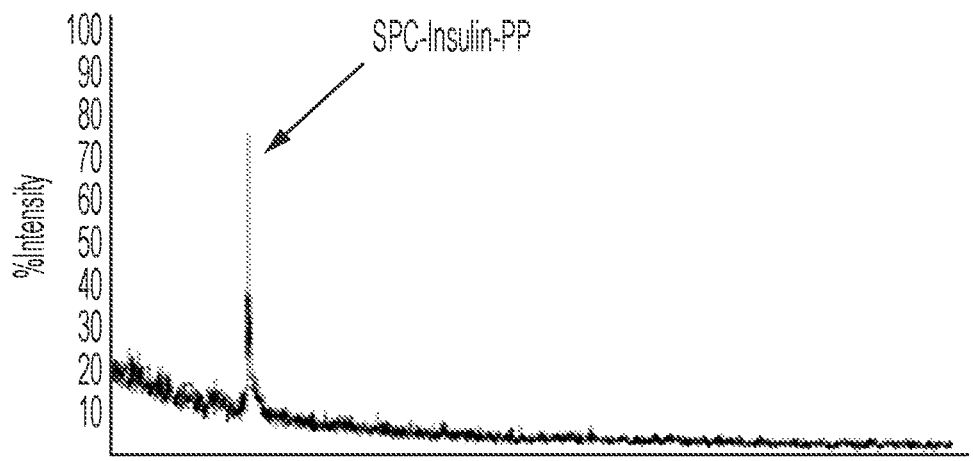
Figure 4B:
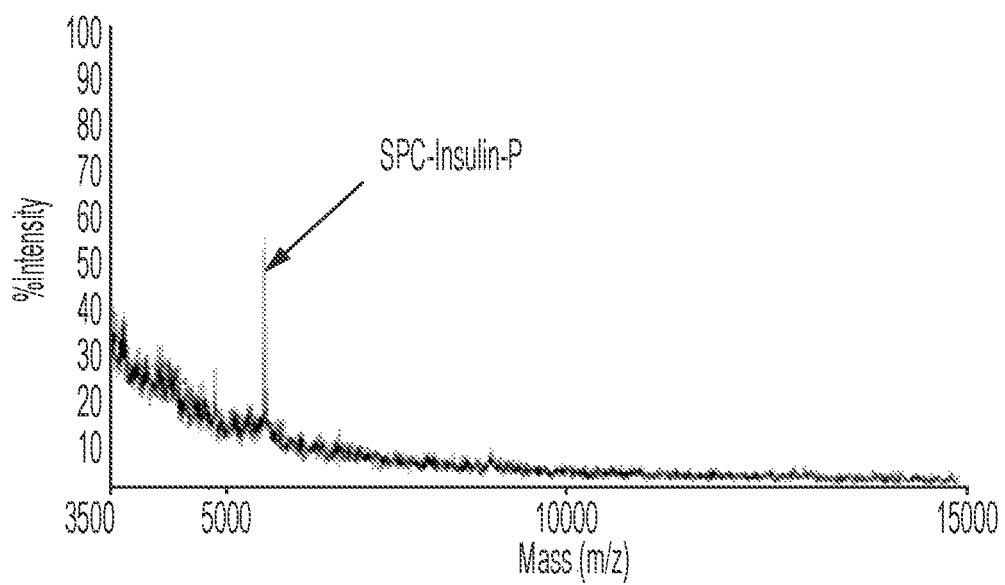
Figure 4C:
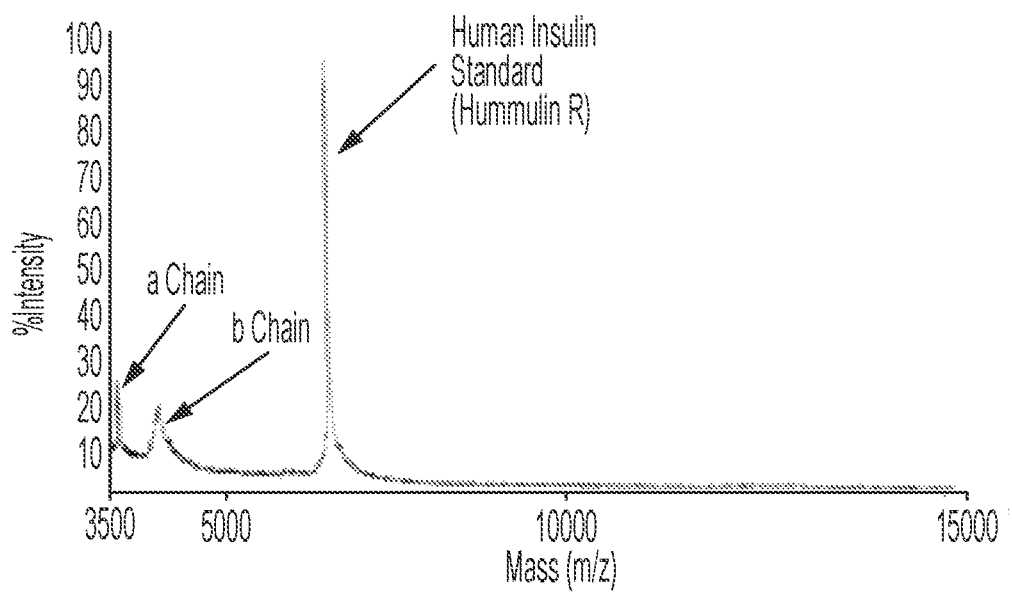
Figure 4D:
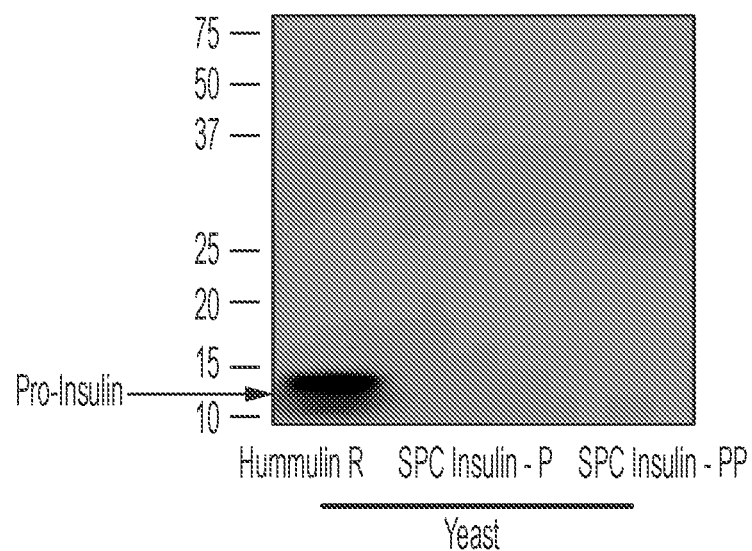

300 ml of each culture medium of the yeast cells transfected with the cDNA of SPC-insulin-P or SPC-insulin-PP were collected and lyophilized. The dried powder was dissolved in distilled water and then passed through a Sephadex-G75 column (1.5×50 cm) using phosphate buffered saline (PBS). The fractions contained the SPC-insulins were confirmed by SDS-PAGE analysis (FIG. 3B), and matrix-assisted laser desorption/ionization-time of flight (MALDI-TOF) mass spectrometry (FIG. 4). The mass spectrometry data also further confirmed that the expressed SPC-insulins are single polypeptide chains having very similar molecular weight with commercial Humulin R (FIG. 4C), and without any contaminations of a- and b- chains. In contrast, small amounts of the inactive a- and b-chains were observed in Humulin R (FIG. 4C), which were resulted from the degradation of the wild-type insulin. In addition, Western blot analysis was used to compare the presence of the proinsulin in the purified insulin solutions between SPC-insulins and Humulin R. No proinsulin in the SCP-insulins were confirmed (FIG. 4D). However, trace amount of proinsulin in Humulin R was observed (FIG. 4C). These results have indicated that the SPC-insulin technology can solve the issues of the unwanted contamination of the inactive proinsulin and a-/b-chains in current recombinant insulin production.

Example 3

Producing of the Engineered SPC-Insulins Using *E. coli* System 3-1. Preparation of *E. coli* Expression Vector.

Figure 2B:
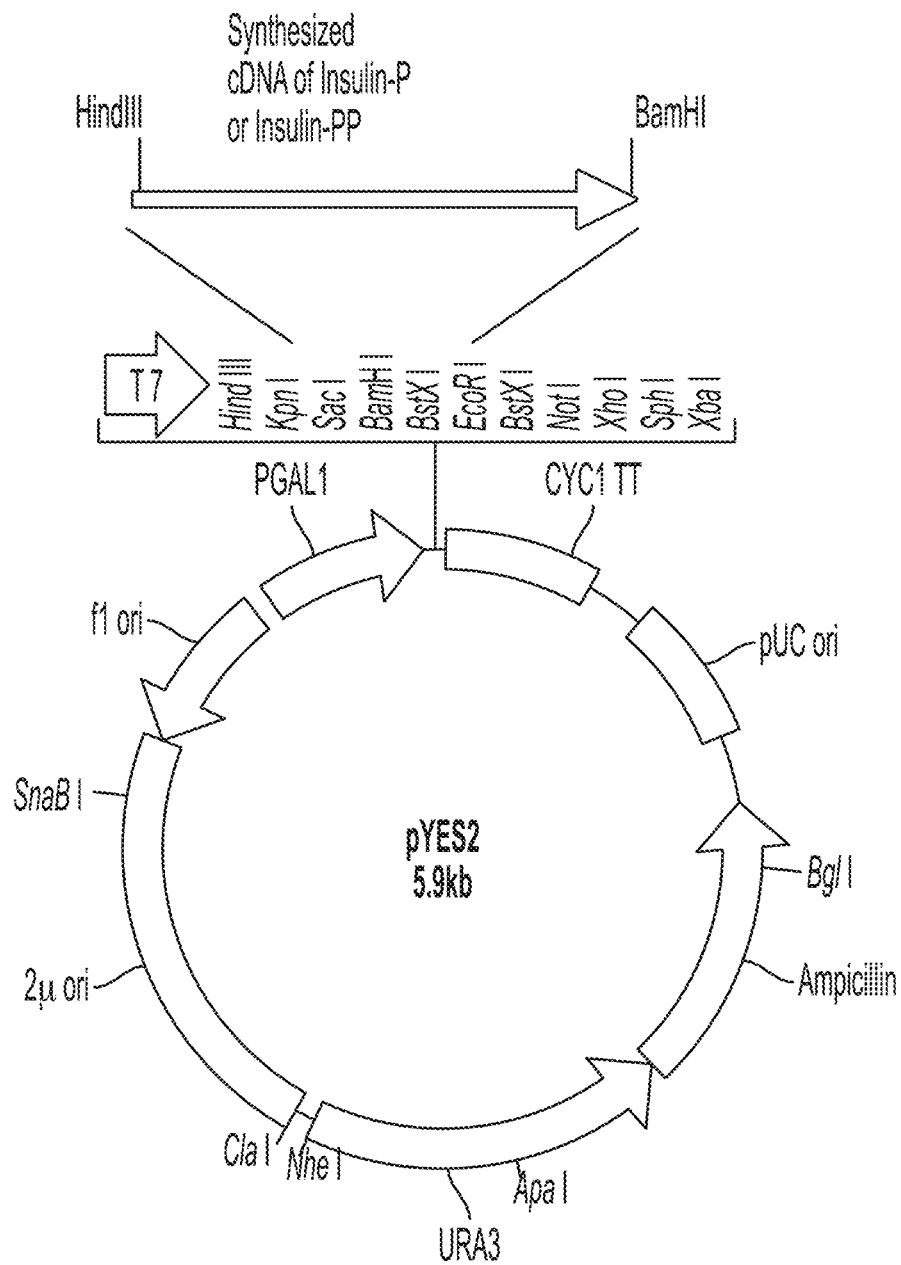

The cDNA of SPC-insulin-P (FIG. 1A) and SPC-insulin-PP (FIG. 1B) were inserted into the cutting sites between Ndel and Xhol of the *E. coli* vector, pET-20b(+) (FIG. 2B). The success cloning was confirmed by DNA sequencing.

3-2. Expression of the SPC-Insulins Using *E. coli* System.

Figure 5A:
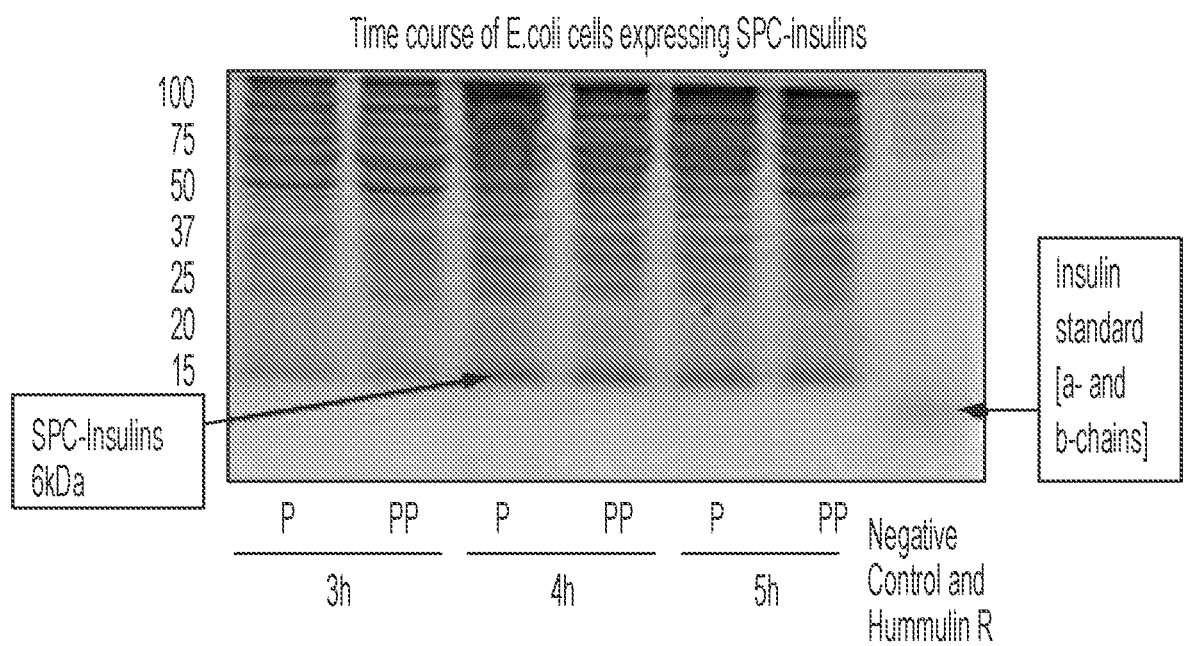

The SPC-insulins are expected to be easily produced using the *E. coli* system similar to that of the yeast system. After transfection of the *E. coli* cells using the pET-20b(+) vector contained the individual cDNAs of the SPC-insulins, the expressed SPC-insulins were monitored. The time course study has showed that the *E. coli* system required only 4-5 hours at 30° C. to express the recombinant SPC-insulins (FIG. 5A). Thus, 4-hour expression was used for further study.

3-3. Extraction of the Expressed SPC-Insulins from *E. coli* Cells.

The *E. coli* cells expressing recombinant SPC-insulins collected from 300 ml culture were homogenized using a glass homogenizer and then sonicated. After centrifugation, the supernatant was collected for ion-exchange purification.

3-4. Ion Exchange Purification.

The extracts of the SPC-insulins from *E. coli* were applied to an ion exchange column using CM-Sepharose (1.0×5 cm). After washing of the column using 20 mM Sodium acetate (NaOAC) buffer pH 4.0, the absorbed SPC-insulins were eluted out by 20 mM NaOAC buffer, pH 4.0 containing 0.5 M NaCl with or without of 20% EtOH.

Example 4

Purification of the SPC-Insulin Using Gel-Filtration Column

Figure 5B:
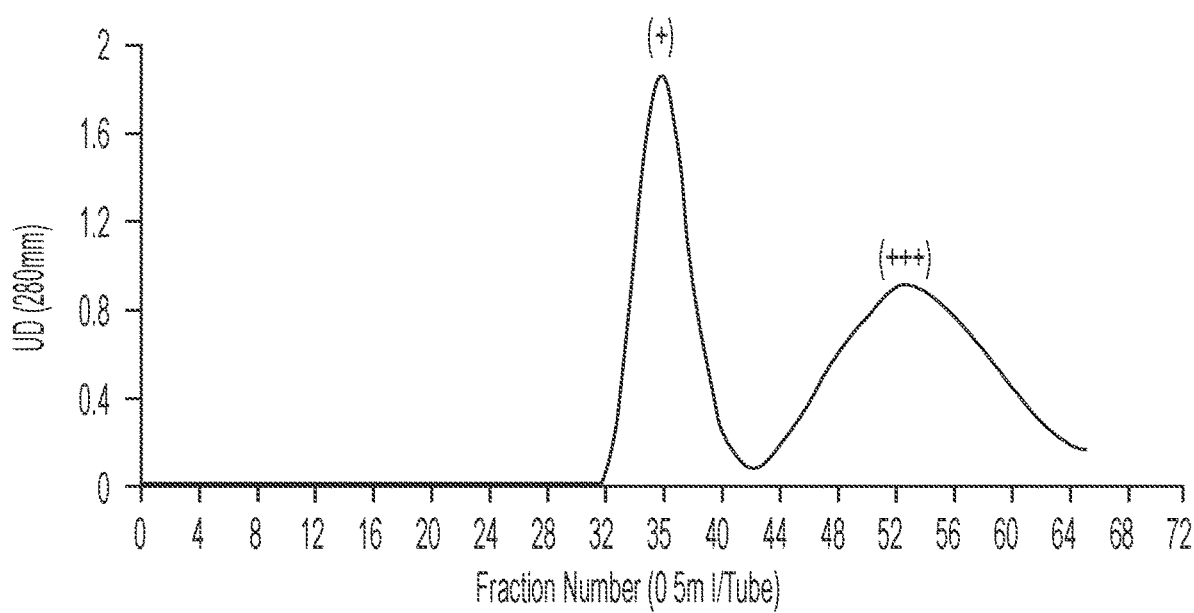
Figure 5C:
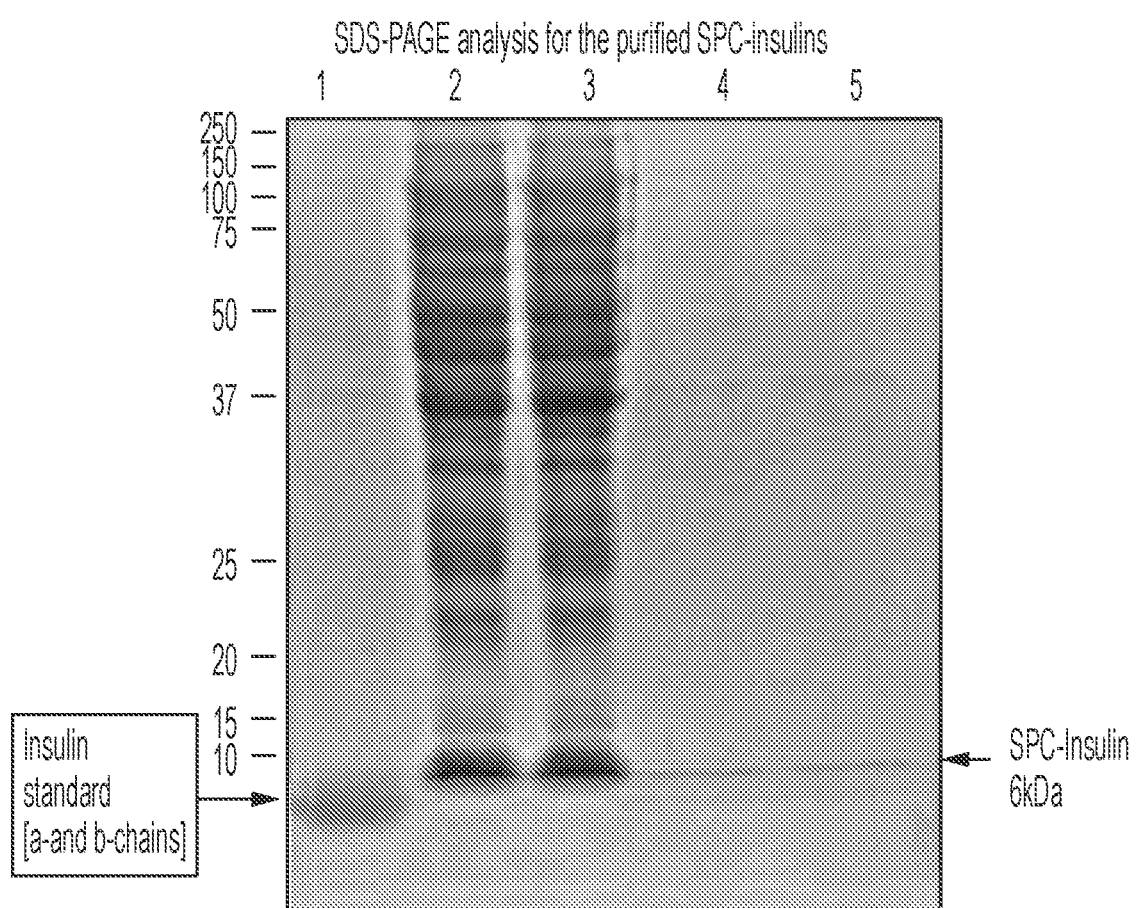

The eluted SPC-insulins from the ion-exchange column were separated by a gel-filtration column, Sephadex-G75 (FIG. 5B). The fractions (second peak) contained the most active SPC-insulins protein were confirmed by PAGE analysis (FIG. 5C), and MOADI mass spectrometry analysis (FIGS. 6A-C). The *E. coli*-expressed SPC-insulins do not contain the a- and b-chains of insulin and proinsulin were also confirmed by the mass spectrometry (FIGS. 6A-B) and Western blot analysis (FIG. 6C).

Example 5

Testing of the Biological Activity Lowering Blood Glucose Level of the SPC-Insulins on Normal Mouse Model Two animal models were used to test the biological activity of the recombinant SPC-insulins. The first model is normal mice. Reducing the animal blood glucose level by the purified yeast- (FIG. 7A) or *E. coli*- (FIG. 7B) expressed-SPC-insulins started around 1-1.5 hour after injections, reached to the best effects around 4 hours and then continually last the effects for 24-48 hours even longer (FIGS. 7A-B). In contrast, the commercial regular insulin, Humulin R could only last 4-8 hours (FIGS. 7A-B). It is the first demonstrating that the SPC-insulins are not only biologically active on lowering blood glucose and also have approximately 3-5-times longer acting duration than that of the regular human insulin (Humulin R), which is currently used to treat patients. This indicates that the SPC-insulins will have much longer therapeutic effects and require only one injection per 24-48 hours on treating diabetes patients. In addition, subcutaneous (FIG. 8A) administrations of the SPC-insulins had similar effects with that of intraperitoneal administration (FIGS. 7A-B) on lowering animal blood glucose levels was also observed.

Example 6

Testing of the Biological Activity Lowering Blood Glucose Level of the SPC-Insulins on STZ-Induced Type-1 Diabetes Mouse Model The second animal model is the STZ-induced type-1 diabetic mouse. The mice received STZ injection quickly developed into type 1 diabetes because STZ destroyed the insulin-producing cells in pancreas and elevated the glucose level (FIGS. 8A-B, blood glucose level labeled with STZ). The both of the purified SPC-insulin-P and -PP were tested on the diabetic mice. Similar to that of the normal mice, the SPC-insulins started working around 1-1.5 hours after injection, reached to the best therapeutic effects around 4 hours, and then last for 24-48 hours (FIGS. 8A-B). This has indicated that the newly engineered SPC-insulins could replace the endogenous insulin to control the hyperglycemia in vivo, and suitable to be developed into a new generation of therapeutic insulin with longer acting and no contamination of inactive proinsulin and degraded a- and b-chain insulin.

Example 7

Conclusions

To avoid the inactivation of insulin by separation of a- and b-chains in circulation, the inventors have fundamentally changed the two-chain property to a single-polypeptide chain, thereby creating SPC-insulins through covalently linking of the a- and b-chains of wild-type insulin using optimized amino-acid residue linkers. The SPC-insulins demonstrate longer acting-duration compared to that of wild-type insulin in vivo and are suitable for further modification into variant insulin analogs for diverse therapeutic uses. On the other hand, the SPC-insulins are still traditional polypeptides, suitable for large-scale recombinant protein production and even transgene therapy. In addition, all of the current recombinant insulin production methods require multiple steps, which include: a) expression of inactive proinsulin, b) purification of the proinsulin, c) cutting the purified proinsulin into active two-chain insulin and inactive C-peptide, and d) purification of the active insulin and removal of the unwanted C-peptide. The SPC-insulins only need two steps to obtain active insulin: a) expression of active SPC-insulins, and b) purification of the SPC-insulins, which has made it easier to produce active insulin and eliminated the contaminations of unwanted/inactive proinsulin and C-peptide in the active insulin preparation.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Aggarwal S R (December 2012). "What's fueling the biotech engine-2011 to 2012". Nature Biotechnology. 30 (12): 1191-97. doi:10.1038/nbt.2437. PMID 23222785.

Baeshen N A, Baeshen M N, Sheikh A, Bora R S, Ahmed M M, Ramadan H A, Saini K S, Redwan E M. Cell factories for insulin production. Microb Cell Fact. 2014 Oct. 2; 13:141. doi: 10.1186/s12934-014-0141-0. Review. PubMed PMID: 25270715; PubMed Central PMCID: PMC4203937.

Brems, D. N., Alter, L. A., Beckage, M. J., Chance, R. E., DiMarchi, R. D., Green, L. K., Long, H. B., Pekar, A. H., Shields, J. E., and Frank, B. H. (1992) Altering the association properties of insulin by amino acid replacement Protein Eng. 5, 527-53320.

Chance R, Frank B. Research, development production and safety of biosynthetic human insulin. Diabetes Care. 1993; 16(3):133-142.

Chance R, Glazer N, Wishner K. Insulin Lispro (Humalog) In: Walsh G, Murphy B, editors. Biopharmaceuticals, an Industrial Perspective. Kluwer: Dordrecht; 1999. pp. 149-172.

Drug Information Portal NLM—Insulin human USAN http://druginfo.nlm nih.gov/drugportal/

Duckworth W C, Bennett R G, Hamel F G (October 1998). "Insulin degradation: progress and potential". Endocrine Reviews. 19 (5): 608-24. doi:10.1210/er.19.5.608. PMID 9793760.

"First Successful Laboratory Production of Human Insulin Announced". News Release. Genentech. 1978-09-06. Retrieved 2016-09-26. https://www.gene.com/media/press-releases/4160/1978-09-06/first-successful-laboratory-production-o Howey D C, Bowsher R R, Brunelle R L, Woodworth J R. Lys (B28), Pro (B29). human insulin: a rapidly absorbed analogue of human insulin. Diabetes 1994; 43(3): 396-402.

Kaur Z P, Ochman A R, Mayer J P, Gelfanov V M, DiMarchi R D. Discovery of high potency, single-chain insulin analogs with a shortened B-chain and nonpeptide linker. ACS Chem Biol. 2013 Aug. 16; 8(8):1822-9. doi: 10.1021/cb4002624. Epub 2013 Jun. 18. PubMed PMID: 23730814

Kjeldsen T. Yeast secretory expression of insulin precursors. Appl Microbiol Biotechnol. 2000; 54:277-286.

Koeslag J H, Saunders P T, Terblanche E (June 2003). "A reappraisal of the blood glucose homeostat which comprehensively explains the type 2 diabetes mellitus-syndrome X complex". The Journal of Physiology (published 2003). 549 (Pt 2): 333-46. doi:10.1113/jphysiol.2002.037895. PMC 2342944 Freely accessible. PMID 12717005

Mudaliar S R, Lindberg F A, Joyce M, et al. Insulin aspart (B28 asp-insulin): a fast-acting analog of human insulin: absorption kinetics and action profile compared with regular human insulin in healthy nondiabetic subjects. Diabetes care 1999; 22(9): 1501-1506

Nakagawa, S. H. and Tager, H. S. (1989) Perturbation of insulin-receptor interactions by intramolecular hormone cross-linking. Analysis of relative movement among residues A1, B1, and B29 J. Biol. Chem. 264,272-279

Palmer B F, Henrich W L. "Carbohydrate and insulin metabolism in chronic kidney disease". UpToDate, Inc.

"The Nobel Prize in Physiology or Medicine 1923". The Nobel Foundation https://www.nobelprize.org/prizes/medicine/1923/summary/

Tof I (1994). "Recombinant DNA technology in the synthesis of human insulin". Little Tree Publishing. Retrieved 2009-11-03.

Voet D, Voet J G (2011). Biochemistry (4th ed.). New York: Wiley.

19th WHO Model List of Essential Medicines (April 2015)" (PDF). WHO. April 2015. Retrieved May 10, 2015. world-wide-web at who.int/medicines/publications/essentialmedicines/EML2015_8-May-15.pdf.

Zion Market Research: "predicted a market for insulin reached to 43.6 billion in 2021," world-wide-web at zionmarketresearch.com/news/global-human-insulin-market.

Angel et al., *Cell,* 49:729, 1987b.
Angel et al., *Mol. Cell. Biol.,* 7:2256, 1987a.
Atchison and Perry, *Cell,* 46:253, 1986.
Atchison and Perry, *Cell,* 48:121, 1987.
Baichwal and Sugden, In: *Gene Transfer*, Kucherlapati (Ed), NY, Plenum Press, 117-148, 1986.
Banerji et al., *Cell,* 27(2 Pt 1):299-308, 1981.
Banerji et al., *Cell,* 33(3):729-740, 1983.
Benvenisty and Neshif, *Proc. Natl. Acad. Sci. USA,* 83:9551-9555, 1986.
Berkhout et al., *Cell,* 59:273-282, 1989.
Blanar et al., *EMBO J.,* 8:1139, 1989.
Bodine and Ley, *EMBO J.,* 6:2997, 1987.
Boshart et al., *Cell,* 41:521, 1985.
Bosze et al., *EMBO J.,* 5(7):1615-1623, 1986.
Braddock et al., *Cell,* 58:269, 1989.
Bulla and Siddiqui, *J. Virol.,* 62:1437, 1986.
Campbell & Villarreal, *Mol. Cell. Biol.,* 8:1993, 1988.
Campere & Tilghman, *Genes and Dev.,* 3:537, 1989.
Campo et al., *Nature,* 303:77, 1983.
Capaldi et al., *Biochem. Biophys. Res. Comm.,* 76:425-433, 1977.
Celander and Haseltine, *J. Virology,* 61:269, 1987.
Celander et al., *J. Virology,* 62:1314, 1988.
Chandler et al., *Cell,* 33:489, 1983.
Chang et al., *Mol. Cell. Biol.,* 9:2153, 1989.
Chatterjee et al., *Proc. Natl. Acad. Sci. USA,* 86:9114, 1989.
Chen and Okayama, *Mol. Cell Biol.,* 7:2745-2752, 1987.
Choi et al., Cell, 53:519, 1988.
Coffin, In: *Virology*, Fields et al. (Eds.), Raven Press, NY, 1437-1500, 1990.
Cohen et al., *J. Cell. Physiol.,* 5:75, 1987.
Cook et al., *Cell,* 27:487-496, 1981.
Costa et al., *Mol. Cell. Biol.,* 8:81, 1988.
Couch et al., *Am. Rev. Resp. Dis.,* 88:394-403, 1963.
Coupar et al., *Gene,* 68:1-10, 1988.
Cripe et al., *EMBO J.,* 6:3745, 1987.
Culotta and Hamer, *Mol. Cell. Biol.,* 9:1376, 1989.
Dandolo et al., *J. Virology,* 47:55-64, 1983.
De Villiers et al., *Nature,* 312(5991):242-246, 1984.
Deschamps et al., *Science,* 230:1174-1177, 1985.
Dubensky et al., *Proc. Natl. Acad. Sci. USA,* 81:7529-7533, 1984.
Edbrooke et al., *Mol. Cell. Biol.,* 9:1908, 1989.
Edlund et al.,*Science,* 230:912-916, 1985.
EP 0273085
Fechheimer et al., *Proc Natl. Acad. Sci. USA,* 84:8463-8467, 1987.
Feng and Holland, *Nature,* 334:6178, 1988.
Ferkol et al., *FASEB J.,* 7:1081-1091, 1993.
Firak and Subramanian, *Mol. Cell. Biol.,* 6:3667, 1986.
Foecking and Hofstetter, *Gene,* 45(1):101-105, 1986.
Fraley et al., *Proc Natl. Acad. Sci. USA,* 76:3348-3352, 1979
Friedmann, *Science,* 244:1275-1281, 1989.

Fujita et al., *Cell*, 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh-Choudhury et al., *EMBO J.*, 6:1733-1739, 1987.
Gilles et al., *Cell*, 33:717, 1983.
Gloss et al., *EMBO J.*, 6:3735, 1987.
Godbout et al., *Mol. Cell. Biol.*, 8:1169, 1988.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Gopal, Mol. Cell Biol., 5:1188-1190, 1985.
Graham and Prevec, In: *Methods in Molecular Biology: Gene Transfer and Expression Protocol*, Murray (Ed.), Humana Press, Clifton, NJ, 7:109-128, 1991.
Graham and van der Eb, *Virology*, 52:456-467, 1973.
Graham et al., *J. Gen. Virol.*, 36:59-72, 1977.
Greene et al., *Immunology Today*, 10:272, 1989
Grosschedl and Baltimore, *Cell*, 41:885, 1985.
Grunhaus and Horwitz, *Seminar in Virology*, 3:237-252, 1992.
Harland and Weintraub, *J. Cell Biol.*, 101:1094-1099, 1985.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Hermonat and Muzycska, *Proc. Nat'l Acad. Sci. USA*, 81:6466-6470, 1984.
Herr and Clarke, *Cell*, 45:461, 1986.
Hersdorffer et al., *DNA Cell Biol.*, 9:713-723, 1990.
Herz and Gerard, *Proc. Nat'l. Acad. Sci. USA* 90:2812-2816, 1993.
Hirochika et al., *J. Virol.*, 61:2599, 1987.
Holbrook et al., *Virology*, 157:211, 1987.
Horlick and Benfield, *Mol. Cell. Biol.*, 9:2396, 1989.
Horwich et al., *J. Virol.*, 64:642-650, 1990.
Huang et al., *Cell*, 27:245, 1981.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Jones and Shenk, *Cell*, 13:181-188, 1978.
Joyce, *Nature*, 338:217-244, 1989.
Kadesch and Berg, *Mol. Cell. Biol.*, 6:2593, 1986.
Kaneda et al., *Science*, 243:375-378, 1989.
Karin et al., *Mol. Cell. Biol.*, 7:606, 1987.
Karlsson et al., *EMBO J.*, 5:2377-2385, 1986.
Katinka et al., *Cell*, 20:393, 1980.
Kato et al., *J Biol Chem.*, 266(6):3361-3364, 1991.
Kawamoto et al., *Mol. Cell. Biol.*, 8:267, 1988.
Kiledjian et al., *Mol. Cell. Biol.*, 8:145, 1988.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kuhl et al., *Cell*, 50:1057, 1987.
Kunz et al., *Nucl. Acids Res.*, 17:1121, 1989.
Larsen et al., *Proc. Natl. Acad. Sci. USA.*, 83:8283, 1986.
Laspia et al., *Cell*, 59:283, 1989.
Latimer et al., *Mol. Cell. Biol.*, 10:760, 1990.
Le Gal La Salle et al., *Science*, 259:988-990, 1993.
Lee et al., *Nature*, 294:228, 1981.
Levinson et al., *Nature*, 295:79, 1982.
Levrero et al., *Gene*, 101:195-202, 1991.
Lin et al., *Mol. Cell. Biol.*, 10:850, 1990.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Majors and Varmus, *Proc. Natl. Acad. Sci. USA*, 80:5866, 1983.
Mann et al., *Cell*, 33:153-159, 1983.
Markowitz et al., *J. Virol.*, 62:1120-1124, 1988.
McNeall et al., *Gene*, 76:81, 1989.
Miksicek et al., *Cell*, 46:203, 1986.
Mordacq and Linzer, *Genes and Dev.*, 3:760, 1989.
Moreau et al., *Nucl. Acids Res.*, 9:6047, 1981.
Muesing et al., *Cell*, 48:691, 1987.
Ng et al., *Nuc. Acids Res.*, 17:601, 1989.
Nicolas and Rubinstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Ondek et al., *EMBO J.*, 6:1017, 1987.
Ornitz et al., *Mol. Cell. Biol.*, 7:3466, 1987.
Palmiter et al., *Cell*, 29:701, 1982.
Palmiter et al., *Nature*, 300:611, 1982.
Paskind et al., *Virology*, 67:242-248, 1975.
Pech et al., *Mol. Cell. Biol.*, 9:396, 1989.
Perales et al., *Proc. Natl. Acad. Sci. USA*, 91(9):4086-4090, 1994.
Perez-Stable and Constantini, *Mol. Cell. Biol.*, 10:1116, 1990.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Racher et al., *Biotech. Techniques*, 9:169-174, 1995.
Ragot et al., *Nature*, 361:647-650, 1993.
Redondo et al., *Science*, 247:1225, 1990.
Reisman and Rotter, *Mol. Cell. Biol.*, 9:3571, 1989.
Remington's Pharmaceutical Sciences, 15th ed., 1035-1038 and 1570-1580, Mack Publishing Company, PA, 1980.
Renan, *Radiother. Oncol.*, 19:197-218, 1990.
Resendez Jr. et al., *Mol. Cell. Biol.*, 8:4579, 1988.
Rich et al., *Hum. Gene Ther.*, 4:461-476, 1993.
Ridgeway, In: *Vectors: A survey of molecular cloning vectors and their uses*, Stoneham: Butterworth, 467-492, 1988.
Ripe et al., *Mol. Cell. Biol.*, 9:2224, 1989.
Rippe et al., *Mol. Cell Biol.*, 10:689-695, 1990.
Rittling et al., *Nuc. Acids Res.*, 17:1619, 1989.
Rosen et al., *Cell*, 41:813, 1988.
Rosenfeld et al., *Cell*, 68:143-155,1992.
Rosenfeld et al., *Science*, 252:431-434,1991.
Roux et al., *Proc. Natl. Acad. Sci. USA*, 86:9079-9083, 1989.

Sakai et al., *Genes and Dev.*, 2:1144, 1988.
Sambrook et al., *Molecular Cloning: A Laboratory Manual*, 2nd Ed., Cold Spring Harbor Press, Cold Spring Harbor, NY, 2001.
Satake et al., *J. Virology*, 62:970, 1988.
Schaffner et al., *J. Mol. Biol.*, 201:81, 1988.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stratford-Perricaudet and Perricaudet, In: *Human Gene Transfer*, Cohen-Haguenauer and Boiron (Eds.), John Libbey Eurotext, France, 51-61, 1991.
Stratford-Perricaudet et al., *Hum. Gene. Ther.*, 1:241-256, 1990.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149-188, 1986.
The Merck Index, 11th Edition.
Thiesen et al., *J. Virology*, 62:614, 1988.
Top et al., *J. Infect. Dis.*, 124:155-160, 1971.
Tronche et al., *Mol. Biol. Med.*, 7:173, 1990.
Trudel and Constantini, *Genes and Dev.* 6:954, 1987.
Tur-Kaspa et al., *Mol. Cell Biol.*, 6:716-718, 1986.
Tyndell et al., *Nuc. Acids. Res.*, 9:6231, 1981.
Vannice and Levinson, *J. Virology*, 62:1305, 1988.
Varmus et al., *Cell*, 25:23-36, 1981.
Vasseur et al., *Proc Natl. Acad. Sci. U.S.A.*, 77:1068, 1980.
Wagner et al., *Proc. Natl. Acad. Sci. USA*, 87(9):3410-3414, 1990.
Wang and Calame, *Cell*, 47:241, 1986.
Weber et al., *Cell*, 36:983, 1984.
Weinberger et al. *Mol. Cell. Biol.*, 8:988, 1984.
Winoto and Baltimore, *Cell*, 59:649, 1989.
Wong et al., *Gene*, 10:87-94, 1980.
Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.
Yang et al., *Proc. Natl. Acad. Sci. USA*, 87:9568-9572, 1990.
Yutzey et al. *Mol. Cell. Biol.*, 9:1397, 1989.
Zelenin et al., *FEBS Lett.*, 280:94-96, 1991.

The invention claimed is:

1. A single chain polypeptide comprising both the b- and a-chain of insulin connected by a 1 or 2 proline amino acid linker, wherein the polypeptide comprises SEQ ID NO: 2 or SEQ ID NO: 4.

2. An expression cassette comprising a nucleic acid encoding a polypeptide of claim 1 under the control of a promoter.

3. The expression cassette of claim 2, wherein the promoter is a bacterial promoter or a eukaryotic promoter.

4. A host cell comprising the expression cassette of claim 2.

5. The host cell of claim 4, wherein the host cell is a bacterial cell.

6. The host cell of claim 4, wherein the host cell is a eukaryotic cell.

7. A method of treating diabetes or hyperglycemia in a subject comprising administering to said subject the single chain polypeptide of claim 1.

8. The method of claim 7, further comprising administering to said subject wild-type insulin.

9. The method of claim 7, wherein said subject is a human, a non-human animal, a dog, a cat, a horse, a cow, a sheep, a rabbit or a mouse.

10. The single chain polypeptide of claim 1, wherein the polypeptide comprises SEQ ID NO: 4.

11. The single chain polypeptide of claim 1, wherein the polypeptide consists of SEQ ID NO: 4.

12. The single chain polypeptide of claim 1, wherein the polypeptide comprises SEQ ID NO: 2.

13. The single chain polypeptide of claim 1, wherein the polypeptide consists of SEQ ID NO: 2.

* * * * *

SEQUENCE LISTING

```
<160> NUMBER OF SEQ ID NOS: 4

<210> SEQ ID NO 1
<211> LENGTH: 166
<212> TYPE: DNA
<213> ORGANISM: Artificial sequence
<220> FEATURE:
<223> OTHER INFORMATION: Synthetic oligonucleotide

<400> SEQUENCE: 1
catatgttcg tgaaccagca tctggtggca gccatctggt ggaggcgctg tatctggtgt      60
gtggcgagcg cggctcttct acactccgaa gactcctggc acgtggagca gtgcgcacca    120
gcatctgcag ccgtatcagc tggagaacta ctgcaactga ctcgag                   166

<210> SEQ ID NO 2
<211> LENGTH: 53
<212> TYPE: PRT
<213> ORGANISM: Artificial sequence
<220> FEATURE:
<223> OTHER INFORMATION: Synthetic polypeptide

<400> SEQUENCE: 2

Met Gly Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Pro
            20                  25                  30

Gly Ile Val Glu Gln Cys Cys Thr Ser Ile Cys Ser Leu Tyr Gln Leu
        35                  40                  45

Glu Asn Tyr Cys Asn
    50

<210> SEQ ID NO 3
<211> LENGTH: 169
<212> TYPE: DNA
```

```
<213> ORGANISM: Artificial sequence
<220> FEATURE:
<223> OTHER INFORMATION: Synthetic oligonucleotide

<400> SEQUENCE: 3
catatgtcgt gaaccagcat ctggtgcagc catctggtgg acgctgtatc tggtgtgtgg      60
cgagcgcggc ttcttctaca ctccgaagac tcctccgggc atcgtggagc agtgctgcac     120
cagcatctgc agcctgtatc agctggagaa ctactgcaac tgactcgag                 169

<210> SEQ ID NO 4
<211> LENGTH: 54
<212> TYPE: PRT
<213> ORGANISM: Artificial sequence
<220> FEATURE:
<223> OTHER INFORMATION: Synthetic polypeptide

<400> SEQUENCE: 4

Met Gly Cys Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Pro
            20                  25                  30

Pro Gly Ile Val Glu Gln Cys Cys Thr Ser Ile Cys Ser Leu Tyr Gln
        35                  40                  45

Leu Glu Asn Tyr Cys Asn
    50
```